US012626169B2

(12) United States Patent
Narain et al.

(10) Patent No.: US 12,626,169 B2
(45) Date of Patent: *May 12, 2026

(54) BAYESIAN CAUSAL RELATIONSHIP NETWORK MODELS FOR HEALTHCARE DIAGNOSIS AND TREATMENT BASED ON PATIENT DATA

(71) Applicant: BPGBio, Inc., Framingham, MA (US)

(72) Inventors: Niven Rajin Narain, Cambridge, MA (US); Viatcheslav R. Akmaev, Sudbury, MA (US); Vijetha Vemulapalli, Westborough, MA (US)

(73) Assignee: BPGbio, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/211,153

(22) Filed: Jun. 16, 2023

(65) Prior Publication Data

US 2024/0169223 A1 May 23, 2024

Related U.S. Application Data

(63) Continuation of application No. 16/592,069, filed on Oct. 3, 2019, now Pat. No. 11,734,593, which is a
(Continued)

(51) Int. Cl.
*G06N 7/01* (2023.01)
*G16H 50/50* (2018.01)
*G16H 50/70* (2018.01)

(52) U.S. Cl.
CPC .............. *G06N 7/01* (2023.01); *G16H 50/50* (2018.01); *G16H 50/70* (2018.01)

(58) Field of Classification Search
CPC ........... G06N 7/01; G16H 50/50; G16H 50/70
See application file for complete search history.

(56) References Cited

U.S. PATENT DOCUMENTS 7,415,359 B2 8/2008 Hill et al.
7,512,497 B2 3/2009 Periwal
(Continued)

FOREIGN PATENT DOCUMENTS

CN 1087187 A 5/1994
CN 1714371 A 12/2005
(Continued)

OTHER PUBLICATIONS

Ayala-Grosso et al., Caspase-3 cleaved spectrin colocalizes with neurofilament-immunoreactive neurons in Alzheimer's disease. Neuroscience. Aug. 25, 2006;141(2):863-874.
(Continued)

*Primary Examiner* — Eric Nilsson
(74) *Attorney, Agent, or Firm* — McCarter & English, LLP; Jill Mello

(57) ABSTRACT

Systems, methods, and computer-readable medium are provided for healthcare analysis. Data corresponding to a plurality of patients is received. The data is parsed to generate normalized data for a plurality of variables, with normalized data generated for more than one variable for each patient. A causal relationship network model is generated relating the plurality of variables based on the generated normalized data using a Bayesian network algorithm. The causal relationship network model includes variables related to a plurality of medical conditions or medical drugs. In another aspect, a selection of a medical condition or drug is received. A sub-network is determined from a causal relationship network model. The sub-network includes one or more variables associated with the selected medical condition or drug. One or more predictors for the selected medical condition or drug are identified.

19 Claims, 25 Drawing Sheets

Related U.S. Application Data continuation of application No. 14/851,846, filed on Sep. 11, 2015, now Pat. No. 10,482,385.

(60) Provisional application No. 62/049,148, filed on Sep. 11, 2014.

(56) References Cited

U.S. PATENT DOCUMENTS

| | | | |
|---|---|---|---|
| 8,000,949 B2 | 8/2011 | Nikolskaya et al. | |
| 8,510,245 B2 | 8/2013 | Stojadinovic et al. | |
| 8,571,803 B2 | 10/2013 | Hill et al. | |
| 9,886,545 B2 | 2/2018 | Narain et al. | |
| 10,061,887 B2 | 8/2018 | Vishnudas et al. | |
| 10,482,385 B2 | 11/2019 | Narain et al. | |
| 11,456,054 B2 | 9/2022 | Narain et al. | |
| 11,734,593 B2 | 8/2023 | Narain et al. | |
| 12,437,835 B2 | 10/2025 | Vishnudas et al. | |
| 2003/0017445 A1 | 1/2003 | Berg et al. | |
| 2006/0019888 A1 | 1/2006 | Zhou | |
| 2007/0038385 A1 | 2/2007 | Nikolskaya et al. | |
| 2007/0134734 A1 | 6/2007 | Endo et al. | |
| 2008/0046290 A1 | 2/2008 | Compton et al. | |
| 2008/0208784 A1 | 8/2008 | Hill et al. | |
| 2008/0294403 A1 | 11/2008 | Zhu et al. | |
| 2009/0144034 A1 | 6/2009 | Simma et al. | |
| 2009/0183268 A1 | 7/2009 | Kingsmore | |
| 2009/0307160 A1 | 12/2009 | Minh et al. | |
| 2010/0125042 A1 | 5/2010 | Geschwind et al. | |
| 2010/0316629 A1 | 12/2010 | Shaughnessy, Jr. et al. | |
| 2011/0027291 A1 | 2/2011 | Schoeberl et al. | |
| 2011/0059861 A1 | 3/2011 | Nolan et al. | |
| 2011/0112380 A1 | 5/2011 | Robinson | |
| 2011/0131027 A1 | 6/2011 | Solomon | |
| 2011/0229483 A1 | 9/2011 | Griffioen et al. | |
| 2011/0294693 A1 | 12/2011 | Hu | |
| 2012/0015838 A1 | 1/2012 | Hu | |
| 2012/0060216 A1 | 3/2012 | Chaudhri et al. | |
| 2012/0070849 A1 | 3/2012 | Perez et al. | |
| 2012/0258874 A1* | 10/2012 | Narain | G16B 5/20 |
| | | | 506/8 |
| 2013/0023574 A1 | 1/2013 | Araki et al. | |
| 2013/0259847 A1 | 10/2013 | Vishnudas et al. | |
| 2013/0275153 A1 | 10/2013 | Dastmalchi et al. | |
| 2013/0315885 A1 | 11/2013 | Narain et al. | |
| 2014/0227693 A1 | 8/2014 | Helgadottir et al. | |
| 2015/0023949 A1 | 1/2015 | Narain et al. | |
| 2018/0275146 A1 | 9/2018 | Narain et al. | |
| 2019/0242909 A1 | 8/2019 | Narain et al. | |
| 2022/0137070 A1 | 5/2022 | Narain et al. | |

FOREIGN PATENT DOCUMENTS

| | | | |
|---|---|---|---|
| CN | 101105841 A | 1/2008 | |
| CN | 101151615 A | 3/2008 | |
| CN | 103493054 A | 1/2014 | |
| CN | 103501859 A | 1/2014 | |
| DE | 102007044380 A1 | 3/2009 | |
| EP | 0590305 A2 | 4/1994 | |
| EP | 1840574 A1 | 10/2007 | |
| EP | 1887351 A1 | 2/2008 | |
| EP | 2600154 A1 | 6/2013 | |
| EP | 2778130 A1 | 9/2014 | |
| EP | 3191975 A1 | 7/2017 | |
| JP | 2005-6563 A | 1/2005 | |
| JP | 2008-65836 A | 3/2008 | |
| JP | 2008-510481 A | 4/2008 | |
| JP | 2008-528975 A | 7/2008 | |
| JP | 2009-50171 A | 3/2009 | |
| JP | 2010-511404 A | 4/2010 | |
| JP | 2011-512163 A | 4/2011 | |
| JP | 2012-500036 A | 1/2012 | |
| JP | 2013-537326 A | 9/2013 | |
| JP | 2014-512520 A | 5/2014 | |
| JP | 2015-503185 A | 1/2015 | |
| WO | 1997/29447 A2 | 8/1997 | |
| WO | 2002/072871 A2 | 9/2002 | |
| WO | 2003/023573 A2 | 3/2003 | |
| WO | 2005/024421 A1 | 3/2005 | |
| WO | 2005/106038 A2 | 11/2005 | |
| WO | 2006/021810 A1 | 3/2006 | |
| WO | 2006/054991 A1 | 5/2006 | |
| WO | 2006/079092 A2 | 7/2006 | |
| WO | 2006/103615 A1 | 10/2006 | |
| WO | 2008/060620 A2 | 5/2008 | |
| WO | 2008/068780 A2 | 6/2008 | |
| WO | 2009/020684 A1 | 2/2009 | |
| WO | 2009/085209 A2 | 7/2009 | |
| WO | 2009/105718 A1 | 8/2009 | |
| WO | 2010/018477 A2 | 2/2010 | |
| WO | 2010/056374 A2 | 5/2010 | |
| WO | 2010/132440 A2 | 11/2010 | |
| WO | 2011/112961 A1 | 9/2011 | |
| WO | 2011/125917 A1 | 10/2011 | |
| WO | 2012/051269 A1 | 4/2012 | |
| WO | 2012/119129 A1 | 9/2012 | |

OTHER PUBLICATIONS

Bandyopadhyay et al., Rewiring of genetic networks in response to DNA damage. Science. Dec. 3, 2010;330(6009):1385-9.

Bignone et al., Phosphorylation of a threonine unique to the short C-terminal isoform of betaII-spectrin links regulation of alpha-beta spectrin interaction to neuritogenesis. J Biol Chem. Jan. 12, 2007;282(2):888-96.

Choudhary et al., Decoding signalling networks by mass spectrometry-based proteomics. Nat Rev Mol Cell Biol. Jun. 2010;11(6):427-39.

Council on Competitiveness High Performance Computing, Bringing the power of HPC to Drug Discovery and the Delivery of "Smarter" Health Care. Case Study. Retrieved online at: http://www.compete.org/images/uploads/File/PDF%20Files/HPC_GNS.pdf. 10 pages, (2010).

Davidson et al., Is hyperglycemia a causal factor in cardiovascular disease? Does proving this relationship really matter? Yes. Diabetes Care. Nov. 2009;32 Suppl 2:S331-3.

De Jong, Modeling and simulation of genetic regulatory systems: a literature review. J Comput Biol. 2002;9(1):67-103.

El Samad et al., Stochastic modelling of gene regulatory networks. Intl J Robust Nonlinear Control. Sep. 2005;15:691-711.

Ferrara et al., Genetic networks of liver metabolism revealed by integration of metabolic and transcriptional profiling. PLoS Genet. Jul. 14, 2008;4(3):e1000034. 13 pages.

Gill et al., A statistical framework for differential network analysis from microarray data. BMC Bioinformatics. Feb. 19, 2010;11:95.

Gregg et al., Gene expression changes in children with autism. Genomics. Jan. 2008;91(1):22-9.

Grimaldi et al., RegnANN: Reverse Engineering Gene Networks using Artificial Neural Networks. PLoS One. Dec. 2011;6(12):e28646. 19 pages.

Hu et al., Gene expression profiling differentiates autism case-controls and phenotypic variants of autism spectrum disorders: evidence for circadian rhythm dysfunction in severe autism. Autism Res. Apr. 2009;2(2):78-97.

Hu et al., Gene expression profiling of lymphoblastoid cell lines from monozygotic twins discordant in severity of autism reveals differential regulation of neurologically relevant genes. BMC Genomics. 2006;7(1):118, 18 pages.

Ideker et al., Differential network biology. Mol Syst Biol. Jan. 17, 2012; 8(565):1-9.

Imoto et al., Computational strategy for discovering druggable gene networks from genome-wide RNA expression profiles. Pac Symp Biocomput. 2006:559-71.

Jeromin et al., Age-related intraneuronal accumulation of II-spectrin breakdown product SBDP-120 in rodent forebrain accelerates in a transgenic model of Alzheimer's Disease: Novel link to neuroplasticity. Neuroscience Meeting Planner, Washington DC: Society for Neuroscience. Poster 48.14/P12, 2 pages, Nov. 12, 2011.

Jorge et al., Statistical model to analyze quantitative proteomics data obtained by 18O/16O labeling and linear ion trap mass spectrom-

(56)          References Cited

OTHER PUBLICATIONS etry: application to the study of vascular endothelial growth factor-induced angiogenesis in endothelial cells. Mol Cell Proteomics. May 2009; 8(5):1130-49.

Lee et al., An integrated approach to infer causal associations among gene expression, genotype variation, and disease. Genomics. Oct. 2009; 94(4):269-77.

Li et al., Large-scale dynamic gene regulatory network inference combining differential equation models with local dynamic Bayesian network analysis. Bioinformatics. Oct. 1, 2011;27(19):2686-91.

Liyan, Study on Data Mining Algorithm and Application. University of Electronic Science and Technology Press, 1st edition. p. 47, Feb. 2013.

PR Newswire, New Company, via Science, Created to Leverage REFS 'Big Data' Supercomputer Technology Across Multiple Industry Applications. Retrieved online at: http://www.prnewswire.com/news-releases/new-company-via-science-created-to-leverage-refs-big-data-supercomputertechnology-across-mu. 2 pages, (Nov. 2010).

Qu et al., The Application of Bayesian Network Model in the Study of TCM Syndrome. Chinese Archives of Traditional Chinese Medicine. Jul. 2008;26(7):1947-1948.

Ratajczak, Theoretical aspects of autism: biomarkers—a review. J Immunotoxicol. Jan.-Mar. 2011;8(1):80-94.

Sachs et al., Causal protein-signaling networks derived from multiparameter single-cell data. Science. Apr. 22, 2005;308(5721):523-9. Erratum in: Science. Aug. 19, 2005;309(5738):1187.

Shannon et al., Cytoscape: a software environment for integrated models of biomolecular interaction networks. Genome Res. Nov. 2003;13(11):2498-504.

Smoot et al., Cytoscape 2.8: new features for data integration and network visualization. Bioinformatics. Dec. 2010;27(3):431-2.

Tomshine et al., Optimization of a stochastically simulated gene network model via simulated annealing. Biophys J. Aug. 2006;91(9):3196-205.

Valcarcel et al., A differential network approach to exploring differences between biological states: an application to prediabetes. PLoS One. Sep. 2011;6(9):e24702. 9 pages.

Van Beijnum et al., Towards high-throughput functional target discovery in angiogenesis research. Trends Mol Med. Jan. 2006; 12(1):44-52.

Veenstra-Vanderweele et al., Networking in autism: leveraging genetic, biomarker and model system findings in the search for new treatments. Neuropsychopharmacology. Jan. 2012;37(1):196-212.

Vujasinovic et al., In silico dynamic molecular interaction networks for the discovery of new therapeutic targets. Curr Pharm Des. 2010;16(20):2241-51.

Wu et al., Multiparameter metabolic analysis reveals a close link between attenuated mitochondrial bioenergetic function and enhanced glycolysis dependency in human tumor cells. Am J Physiol Cell Physiol. Jan. 2007;292(1):C125-36.

Xing et al., Causal modeling using network ensemble simulations of genetic and gene expression data predicts genes involved in rheumatoid arthritis. PLoS Comput Biol. Mar. 2011;7(3):e1001105.

Zhang, Foundations of Computational Intelligence. Harbin Engineering University Press. p. 147, Mar. 31, 2001.

Chinese Office Action for Application No. 201580058049.5, dated Mar. 1, 2021, with English translation, 61 pages.

* cited by examiner

300

302
RECEIVE DATA CORRESPONDING TO PATIENTS

304
PARSE DATA TO GENERATE NORMALIZED DATA

306
GENERATE A CAUSAL RELATIONSHIP NETWORK MODEL

400

402 RECEIVE INFORMATION FROM USER

404 DETERMINE SUB-NETWORK FROM A CAUSAL RELATIONSHIP NETWORK MODEL

406 TRAVERSE THE SUB-NETWORK TO IDENTIFY PREDICTORS

408 STORE THE PREDICTORS

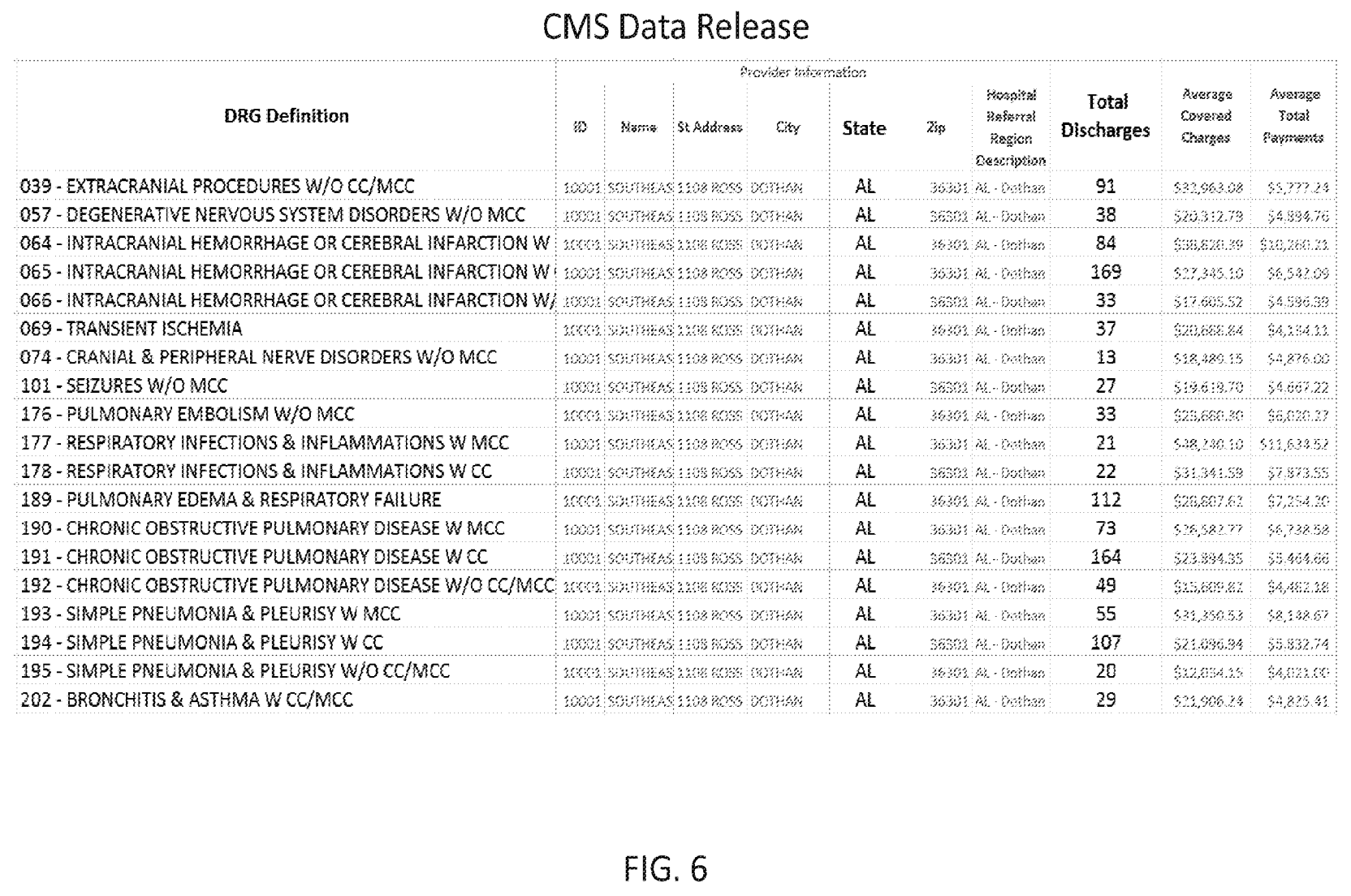

CMS Data Release

| DRG Definition | Provider Information | | | | | | | Total Discharges | Average Covered Charges | Average Total Payments |
|---|---|---|---|---|---|---|---|---|---|---|
| | ID | Name | St. Address | City | State | Zip | Hospital Referral Region Description | | | |
| 039 - EXTRACRANIAL PROCEDURES W/O CC/MCC | | | | DOTHAN | AL | | | 91 | | |
| 057 - DEGENERATIVE NERVOUS SYSTEM DISORDERS W/O MCC | | | | DOTHAN | AL | | | 38 | | |
| 064 - INTRACRANIAL HEMORRHAGE OR CEREBRAL INFARCTION W | | | | DOTHAN | AL | | | 84 | | |
| 065 - INTRACRANIAL HEMORRHAGE OR CEREBRAL INFARCTION W | | | | DOTHAN | AL | | | 169 | | |
| 066 - INTRACRANIAL HEMORRHAGE OR CEREBRAL INFARCTION W/ | | | | DOTHAN | AL | | | 33 | | |
| 069 - TRANSIENT ISCHEMIA | | | | DOTHAN | AL | | | 37 | | |
| 074 - CRANIAL & PERIPHERAL NERVE DISORDERS W/O MCC | | | | DOTHAN | AL | | | 13 | | |
| 101 - SEIZURES W/O MCC | | | | DOTHAN | AL | | | 27 | | |
| 176 - PULMONARY EMBOLISM W/O MCC | | | | DOTHAN | AL | | | 33 | | |
| 177 - RESPIRATORY INFECTIONS & INFLAMMATIONS W MCC | | | | DOTHAN | AL | | | 21 | | |
| 178 - RESPIRATORY INFECTIONS & INFLAMMATIONS W CC | | | | DOTHAN | AL | | | 22 | | |
| 189 - PULMONARY EDEMA & RESPIRATORY FAILURE | | | | DOTHAN | AL | | | 112 | | |
| 190 - CHRONIC OBSTRUCTIVE PULMONARY DISEASE W MCC | | | | DOTHAN | AL | | | 73 | | |
| 191 - CHRONIC OBSTRUCTIVE PULMONARY DISEASE W CC | | | | DOTHAN | AL | | | 164 | | |
| 192 - CHRONIC OBSTRUCTIVE PULMONARY DISEASE W/O CC/MCC | | | | DOTHAN | AL | | | 49 | | |
| 193 - SIMPLE PNEUMONIA & PLEURISY W MCC | | | | DOTHAN | AL | | | 55 | | |
| 194 - SIMPLE PNEUMONIA & PLEURISY W CC | | | | DOTHAN | AL | | | 107 | | |
| 195 - SIMPLE PNEUMONIA & PLEURISY W/O CC/MCC | | | | DOTHAN | AL | | | 20 | | |
| 202 - BRONCHITIS & ASTHMA W CC/MCC | | | | DOTHAN | AL | | | 29 | | |

FIG. 6

C.O.P.D → Low oxygen concentration in blood → Pulmonary hypertension → Strain on right ventricle → Heart failure Fourfold Plot – Heart Failure with Renal Failure Relative Risk = 2.57

Fourfold Plot – Heart Failure with G I Hemorrhage

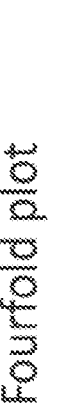
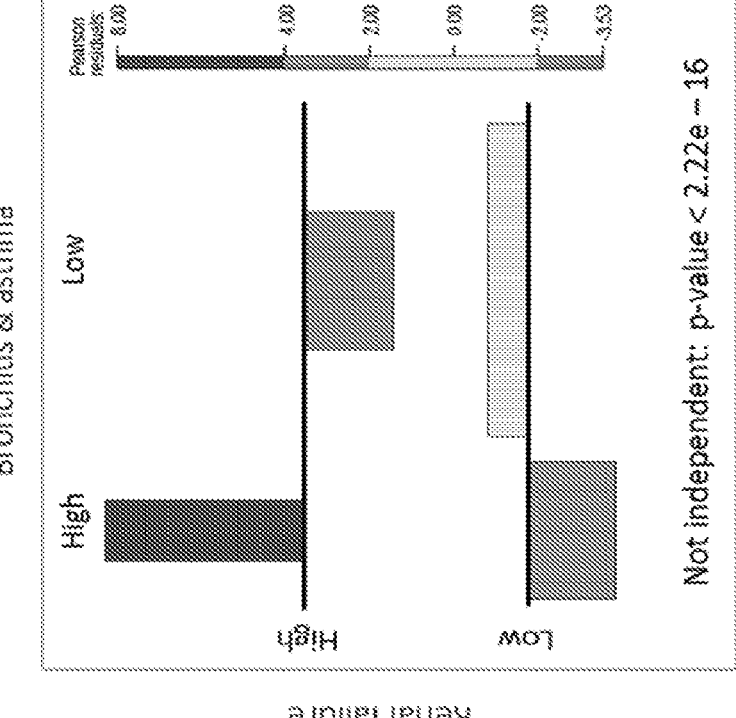
Fourfold plot
Bronchitis & asthma: high
Renal failure: low
46
431
Bronchitis & asthma: low
46
47
Renal failure: high
Relative Risk = 5.13
(Renal failure with bronchitis & asthma)
FIG. 18B
Association plot
Bronchitis & asthma
High    Low
High
Low
Renal failure
Pearson
residuals
Not independent: p-value < 2.22e − 16
FIG. 18A

BAYESIAN CAUSAL RELATIONSHIP NETWORK MODELS FOR HEALTHCARE DIAGNOSIS AND TREATMENT BASED ON PATIENT DATA

RELATED APPLICATION

This application is a continuation of U.S. patent application Ser. No. 16/592,069, filed Oct. 3, 2019, which, in turn, is a continuation of U.S. patent application Ser. No. 14/851, 846, filed Sep. 11, 2015, which, in turn, claims benefit of and priority to U.S. Provisional Patent Application No. 62/049, 148 filed on Sep. 11, 2014, the entire disclosure of each application is incorporated herein by reference in its entirety.

TECHNICAL FIELD

The present disclosure relates generally to systems and methods for data analysis, in particular, for using healthcare data to generate a causal relationship network model.

BACKGROUND

Many systems analyze data to gain insights into various aspects of healthcare. Insights can be gained by determining relationships among the data. Conventional methods predetermine a few relevant variables to extract from healthcare data for processing and analysis. Based on the few preselected variables, relationships are established between various factors such as medical drug, disease, symptoms, etc. Preselecting the variables to focus on limits the ability to discover new or unknown relationships. Preselecting the variables also limits the ability to discover other relevant variables. For example, if the variables are preselected when considering analysis of diabetes, one would be limited to those variables and not realize that the data analysis supports another variable relevant to diabetes that was previously unknown to the healthcare community.

SUMMARY

In one aspect, the invention relates to a computer-implemented method for generating a causal relationship network model based on patient data. The method includes receiving data corresponding to a plurality of patients, where the data includes diagnostic information and/or treatment information for each patient, parsing the data to generate normalized data for a plurality of variables, wherein, for each patient, the normalized data is generated for more than one variable, generating a causal relationship network model relating the plurality of variables based on the generated normalized data using a Bayesian network algorithm, the causal relationship network model includes variables related to a plurality of medical conditions, and the causal relationship network generated using a programmed computing system including storage holding network model building code and one or more processors configured to execute the network model building code.

In certain embodiments, the causal relationship network model includes relationships indicating one or more predictors for each of the plurality of medical conditions. In certain embodiments, the data received is not pre-selected as being relevant to one or more of the plurality of medical conditions. In some embodiments, the method further includes receiving additional data corresponding to one or more additional patients, and updating the causal relationship network model based on the additional data. In certain embodiments, the causal relationship network model is generated based solely on the generated normalized data.

In some embodiments, the method further includes determining a sub-network from the causal relationship network model, one or more variables in the sub-network associated with a selected medical condition, and probing relationships in the sub-network to determine one or more predictors for the selected medical condition. In certain embodiments, the one or more predictors for the selected medical condition indicate a medical condition co-occurring with the selected medical condition. In certain embodiments, the extent of the sub-network is determined based on the one or more variables associated with the selected medical condition and the strength of the relationships between the one or more variables and other variables in the causal relationship network model. In certain embodiments, the sub-network includes the one or more variables associated with the selected medical condition, a first set of additional variables each having a first degree relationship with the one or more variables, and a second set of additional variables each having second degree relationship with the one or more variables. In some embodiments, at least one of the one or more predictors is previously unknown. In some embodiments, at least one of the one or more predictors is newly identified as a predictor for the medical condition. In certain embodiments, the number of predictors is less than the number of variables.

In some embodiments, the method further includes displaying the one or more predictors in a user interface, the displaying including a graphical representation of the one or more variables, the one or more predictors, and relationships among the one or more variables and the one or more predictors. In some embodiments, the method further includes displaying a graphical representation of the sub-network in a user interface. In some embodiments, the method further includes ranking the one or more predictors based on strength of relationships between the one or more variables and the one or more predictors.

In certain embodiments, the method further includes determining a sub-network from the causal relationship network model, one or more variables in the sub-network associated with a selected drug, and probing the sub-network to determine one or more predictors relevant to the selected drug. In some embodiments, the one or more predictors relevant to the selected drug indicate a drug administered in conjunction with the selected drug. In some embodiments, the one or more predictors indicate an adverse drug interaction between the selected drug and one or more other drugs. In some embodiments, the extent of the sub-network is determined based on the one or more variables associated with the selected drug and the strength of the relationships between the one or more variables and other variables in the causal relationship network model. In some embodiments, the sub-network includes the one or more variables associated with the selected drug, a first set of additional variables each having a first degree relationship with the one or more variables, and a second set of additional variables each having second degree relationship with the one or more variables. In other embodiments, at least one of the one or more predictors is previously unknown. In some embodiments, at least one of the one or more predictors is newly identified as a predictor for the medical condition. In other embodiments, the number of predictors is less than the number of variables.

In certain embodiments, the causal relationship network model is generated based on at least 50 variables.

In certain embodiments, the causal relationship network model is generated based on at least 100 variables.

In certain embodiments, the causal relationship network model is generated based on at least 1000 variables.

In certain embodiments, the causal relationship network model is generated based on at least 100,000 variables.

In certain embodiments, the causal relationship network model is generated based on between 50 variables and 1,000,000 variables.

In other embodiments, the causal relationship network is generated based on data from between 50 patients and 1,000,000 patients.

In other embodiments, the data includes information from patient electronic health records.

In certain embodiments, the received data further includes at least one of: patient demographics, medical history, patient family medical history, active medication information, inactive past medication information, allergy information, immunization status information, laboratory test results, radiology images, vital sign information, patient weight, billing information, life style information, habits information, insurance claims information, and pharmacy information, for at least some of the plurality of patients. In some embodiments, the patient demographics include at least one of patient age, patient race, and patient ethnicity.

In certain embodiments, the received data includes information from patient chart. In some embodiments, the information from the patient chart includes at least one of notes by a health care professional, observations by a health care professional, administration of drugs and therapies, orders for the administration of drugs and therapies, test results, and x-rays.

In certain embodiments, the received data includes patient discharge information. In some embodiments, the patient discharge information includes at least one of a diagnosis code, a treatment code, an insurance charge code, a diagnosis-related group code, and an International Classification of Diseases code.

In certain embodiments, the received data relates to a plurality of patients from a selected hospital. In certain embodiments, the received data relates to a plurality of patients from a selected geographic area.

In some embodiments, generating the causal relationship network model relating the variables for the plurality of patients based on the generated normalized data using a Bayesian network algorithm comprises creating a library of network fragments based on the variables via a Bayesian Fragment Enumeration process, creating an ensemble of trial networks, each trial network constructed from a different subset of the network fragments in the library, and globally optimizing the ensemble of trial networks by evolving each trial network through local transformations via simulated annealing to produce a consensus causal relationship network model. In some embodiments, generating the causal relationship network model relating the variables for the plurality of patients based on the generated normalized data using a Bayesian network algorithm further comprises in silico simulation of the consensus causal relationship network model based on input data, to provide a confidence level of prediction for one or more causal relationships within the resulting causal relationship network model.

In another aspect, the invention relates to a computer-implemented method for using a causal relationship network model. The method includes receiving a selection of a medical condition from a plurality of medical conditions, determining a sub-network from a computer generated causal relationship network model, the causal relationship network model generated from patient data using a Bayesian network algorithm and comprising a plurality of variables including variables related to the plurality of medical conditions, the causal relationship network model based on the selected medical conditions, the sub-network including one or more variables associated with the selected medical condition, traversing the sub-network to identify one or more predictors for the selected medical condition, and storing the one or more predictors for the selected medical condition.

In certain embodiments, the selection of the medical condition is received from a user via a user interface. In some embodiments, at least one of the one or more predictors is previously unknown. In some embodiments, at least one of the one or more predictors is newly identified as a predictor for the medical condition. In some embodiments, the number of predictors is less than the number of variables.

In some embodiments, the method further includes applying a regression algorithm to the predictors to determine a relationship of each predictor to the selected medical condition or drug. In some embodiments, the method further includes displaying the predictors in the user interface, the displaying including a graphical representation of the one or more selected variables, the one or more predictors, and relationships among the one or more selected variables and the predictors. In some embodiments, the method further includes displaying a graphical representation of the sub-network in the user interface. In some embodiments, the method further includes ranking the one or more predictors based on strength of relationships between the one or more selected variables and the one or more predictors.

In certain embodiments, the one or more predictors are associated with one or more medical drugs. In certain embodiments, the predictors are associated with one or more medical conditions.

In another aspect, the invention relates to a computer-implemented method for using a causal relationship network model. The method includes receiving a query associated with a medical condition from a plurality of medical conditions, determining a sub-network from a computer generated causal relationship network model, the causal relationship network model generated from patient data using a Bayesian network algorithm and comprising a plurality of variables including variables related to the plurality of medical conditions, the causal relationship network model based on the queried medical condition, the sub-network including one or more variables associated with the queried medical condition, traversing the sub-network to identify one or more predictors for the queried medical condition, and storing the one or more predictors for the queried medical condition. In certain embodiments, the query received from the user includes information associated with a medical condition and/or a medical drug.

In another aspect, the invention relates to a computer-implemented method for using a causal relationship network model. The method includes receiving information associated with a medical drug, determining a sub-network from a computer generated causal relationship network model, the causal relationship network model generated from patient data using a Bayesian network algorithm and comprising a plurality of variables including variables related to the plurality of medical drugs, the causal relationship network model based on the medical drug, the sub-network including one or more variables associated with the medical drug, traversing the sub-network to identify one or more predictors for the medical drug, and storing the one or more predictors for the medical drug.

In yet another aspect, the invention relates to a system for generating a causal relationship network model based on patient data. The system includes a data-receiving module configured to receive data related to a plurality of patients, the data including diagnostic information and/or treatment information for each patient, a parsing module configured to parse the data to generate normalized data for a plurality of variables, wherein, for each patient, the normalized data is generated for more than one variable, and a processor-implemented relationship-network module configured to generate a causal relationship network model relating the plurality of variables based on the generated normalized data using a Bayesian network algorithm, the causal relationship network model including variables related to a plurality of medical conditions. In certain embodiments, the causal relationship network model includes relationships indicating one or more predictors for each of the plurality of medical conditions.

In yet another aspect, the invention provides a system for using a causal relationship network model based on patient data. The system includes a data-receiving module configured to receive information associated with a medical condition, a sub-network module configured to determine a sub-network from a computer generated causal relationship network model, the causal relationship network model generated from patient data using a Bayesian network algorithm and comprising a plurality of variables including variables related to a plurality of medical conditions, the causal relationship network model based on the medical condition, the sub-network including one or more variables associated with the medical condition, and a variable identification module configured to traverse the sub-network and identify one or more predictors for the medical condition. In certain embodiments, the computer-generated causal relationship network model is generated using the disclosed methods of certain embodiments.

In yet another aspect, the invention provides a non-transitory machine readable storage medium storing at least one program that, when executed by at least one processor, causes the at least one processor to perform any methods disclosed as part of certain embodiments.

In another aspect, the invention provides a system for generating predictors for a medical condition. The system includes a causal relationship network model generator configured to receive data corresponding to a plurality of patients, the data including diagnostic information and/or treatment information for each patient, parse the data to generate normalized data for a plurality of variables, wherein, for each patient, the normalized data is generated for more than one variable, and generate a causal relationship network model relating each variable to one or more of the plurality of variables based on the generated normalized data using a Bayesian network algorithm, the causal relationship network model including variables related to a plurality of medical conditions. In certain embodiments, the causal relationship network model includes relationships indicating one or more predictors for each of the plurality of medical conditions. In some embodiments, the system further includes a sub-network selection module configured to receive information associated with a medical condition from a user via a user interface, determine a sub-network from the causal relationship network model, the sub-network including one or more variables related to the medical condition, traverse the sub-network to identify one or more predictors for the medical condition, and store the one or more predictors for the medical condition.

In another aspect, the invention provides a system for generating a causal relationship network model based on patient data. The system includes a data receiving module, implemented by a first processor, configured to receive data correspond to a plurality of patients, the data including diagnostic information and/or treatment information for each patient, and parse the data to generate normalized data for a plurality of variables, wherein, for each patient, the normalized data is generated for more than one variable, and a causal relationship network module, implemented by a one or more additional processors, configured to generate a causal relationship network model relating the plurality of variables based on the generated normalized data using a Bayesian network algorithm, the causal relationship network model including variables related to a plurality of medical conditions.

Throughout the present application, all values presented in a list, e.g., such as those above, can also be the upper or lower limit of ranges that are intended to be a part of this invention.

BRIEF DESCRIPTION OF FIGURES

The present disclosure is illustrated by way of example, and not limitation, in the figures of the accompanying drawings, in which like reference numerals indicate similar elements unless otherwise indicated.

FIG. 6 is an example dataset from a healthcare entity used in Example 1.

FIG. 18A is an association plot of renal failure with bronchitis and asthma generated from the relationship network model in Example 1.

FIG. 18B is a fourfold plot of renal failure with bronchitis and asthma generated from the relationship network model in Example 1.

DETAILED DESCRIPTION OF EXEMPLARY EMBODIMENTS

Figure 1:
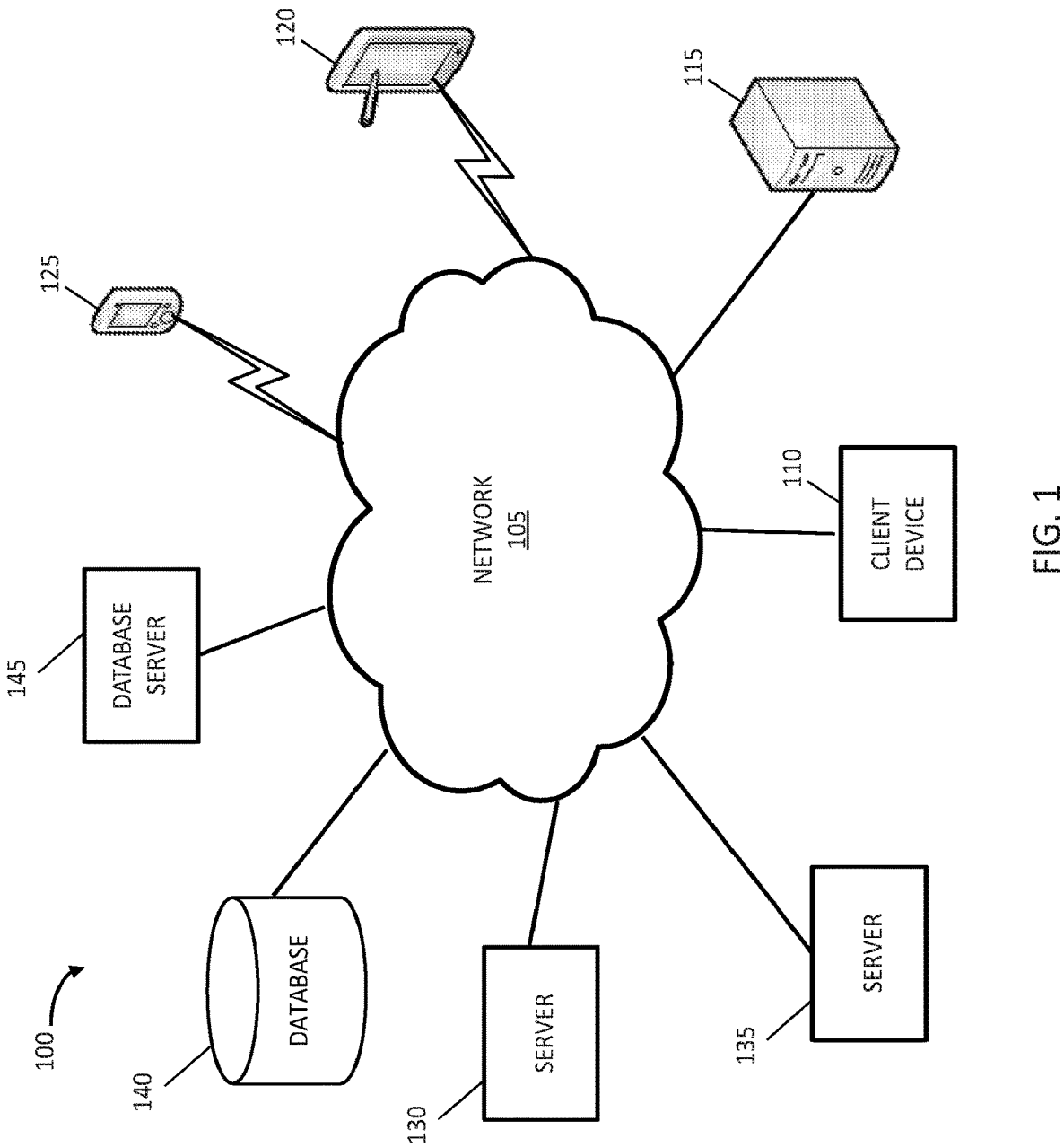
FIG. 1 is a schematic network diagram depicting a system for healthcare analysis, according to an embodiment.

In recent years there has been a quantum explosion in healthcare data since the drive to adopt electronic health records. This healthcare data can be leveraged to open up new avenues in advancing healthcare by improving patient care and creating new efficiencies in delivering care. For example, understanding variation in treatment outcomes due to patient specific molecular and clinical factors may enable creation of precision models in medicine.

Predominant foci of big data efforts in health care have been better management and curation of health care data, and data mining to test hypotheses. Conventional analysis of health data has been limited by reliance on long-held biological or clinical phenotype hypotheses, or other assumptions underlying the analysis.

Embodiments described herein include systems, methods, and computer readable-medium for healthcare analysis.

Some embodiments generate a causal relationship network model based on data related to various areas of healthcare, such as patient care, using a Bayesian network algorithm. The data used to generate the relationship network model is a large collection of data that has not be pre-selected or pre-filtered for relevance. Further, generation of the causal relationship network model does not rely on assumptions regarding which variables are relevant or irrelevant, or prior knowledge regarding relationships between the variables. This unbiased approach enables embodiments of methods and system to build a network model that depicts connections supported by the collection of data, and is that unbiased by known clinical research. Thus, in contrast to conventional approaches in which data is preselected for relevance and that involve prior knowledge regarding relationships between variables, the resulting network of some embodiments may be more likely to include novel interactions between variables that were previously unknown to the healthcare community, or that were not previously researched or explored by the healthcare community. Some embodiments involve methods and systems for modeling patient data that are completely data-driven and unbiased by current knowledge. Such data-driven and unbiased models can be used for discovery of new and often surprising trends in disease outcomes. Some embodiments can be used to identify non-obvious comorbidities, and develop improved treatment strategies and protocols.

In some embodiments, data is obtained or received that includes healthcare-related information. The received data is processed and parsed to generate normalized data for a plurality of variables. A causal relationship network model is generated based on the variables using a Bayesian network algorithm. In some instances, the relationship network model includes a plurality of medical conditions and a plurality of medical drugs, and indicates the relationship between the medical conditions and drugs.

Some embodiments include methods for using a generated causal relationship network model. For example, some embodiments include receiving information from a user that relates to a medical condition or medical drug. Based on the received information, a sub-network is determined from the generated causal relationship network model. The sub-network is traversed or probed to determine predictors for the medical condition or drug of interest. A predictor may be a significant factor having an effect on the medical condition or drug.

Definitions

As used herein, certain terms intended to be specifically defined, but are not already defined in other sections of the specification, are defined herein.

The term "diagnostic/treatment information" refers to any information encoding a diagnosis made or information describing which treatments were provided.

The term "medical condition" refers to any pathological condition, disease, and/or illness affecting a person that may present symptoms and signs.

The term "medical drug" or "drug" refers to any medicine, medication, therapeutic agent, and/or chemical substance that may be used in curing, treating, and/or preventing a medical condition, and/or in diagnosing a medical condition.

The term "predictor" refers to a variable that can be employed in a mathematical equation, algorithm or decision support tool to predict an outcome. A mathematical equation, algorithm or decision support tool may employ multiple predictors for predicting an outcome.

The following description is presented to enable any person skilled in the art to create and use systems and methods for healthcare analysis. Various modifications to embodiments will be readily apparent to those skilled in the art, and the generic principles defined herein may be applied to other embodiments and applications without departing from the spirit and scope of the invention. Moreover, in the following description, numerous details are set forth for the purpose of explanation. However, one of ordinary skill in the art will realize that the invention may be practiced without the use of these specific details. In other instances, well-known structures and processes are shown in block diagram form in order not to obscure the description of the invention with unnecessary detail. Thus, the present disclosure is not intended to be limited to the embodiments shown, but is to be accorded the widest scope consistent with the principles and features disclosed herein.

FIG. 1 illustrates a network diagram depicting an example system 100 that may be included in part or in full in a healthcare analysis system in accordance with an embodiment. The system 100 can include a network 105, a client device 110, a client device 115, a client device 120, a client device 125, a server 130, a server 135, a database(s) 140, and a database server(s) 145. Each of the client devices 110, 115, 120, 125, server 130, server 135, database(s) 140, and database server(s) 145 is in communication with the network 105.

In an embodiment, one or more portions of network 105 may be an ad hoc network, an intranet, an extranet, a virtual private network (VPN), a local area network (LAN), a wireless LAN (WLAN), a wide area network (WAN), a wireless wide area network (WWAN), a metropolitan area network (MAN), a portion of the Internet, a portion of the Public Switched Telephone Network (PSTN), a cellular telephone network, a wireless network, a WiFi network, a WiMax network, any other type of network, or a combination of two or more such networks.

Examples of a client device include, but are not limited to, work stations, personal computers, general purpose computers, Internet appliances, laptops, desktops, multi-processor systems, set-top boxes, network PCs, wireless devices, portable devices, wearable computers, cellular or mobile phones, portable digital assistants (PDAs), smartphones, tablets, ultrabooks, netbooks, multi-processor systems, microprocessor-based or programmable consumer electronics, mini-computers, and the like. Each of client devices 110, 115, 120, 125 may connect to network 105 via a wired or wireless connection.

In an example embodiment, the healthcare analysis system included on the client device 110, 115, 120, 125 may be configured to locally perform some of the functionalities described herein, while the server 130, 135 performs the other functionalities described herein. For example, the client device 110, 115, 120, 125 may receive patient data and parse the patient data, while the server 135 may generate the causal relationship network. In another example, the client device 110, 115, 120, 125, may receive a selection of criteria, while the server 135 may determine a sub-network from a causal relationship network, traverse the sub-network to identify predictors for the selected criteria, and store the identified predictors. In yet another example, the client device 110, 115, 120, 125 may receive a selection of criteria, the server 135 may determine a sub-network from a causal relationship network and traverse the sub-network to identify predictors for the selected criteria, and the client device 110, 115, 120, 125 may store the identified predictors.

In an alternative embodiment, the client device 110, 115, 120, 125 can perform all the functionalities described herein. For example, the client device 110, 115, 120, 125 may receive patient data, parse the patient data, and generate a causal relationship network based on the patient data. In another example, the client device 110, 115, 120, 125 may receive a selection of criteria, for example, medical condition or a medical drug, determine a sub-network from a causal relationship network based on the selected criteria, traverse the sub-network to identify predictors for the selected criteria, and store the identified predictors.

In another alternative embodiment, the healthcare analysis system may be included on the client device 110, 115, 120, 125, and the server 135 performs the functionalities described herein. For example, the server 135 may receive patient data, parse the patient data, and generate a causal relationship network based on the patient data. In another example, the server 135 may receive a selection of a criteria, for example, a medical condition or a medical drug, determine a sub-network from a causal relationship network based on the selected criteria, traverse the sub-network to identify predictors for the selected criteria, and store the identified predictors.

In some embodiments, server 130 and server 135 may be part of a distributed computing environment, where some of the tasks/functionalities are distributed between servers 130 and 135. In some embodiments, server 130 and server 135 are part of a parallel computing environment, where server 130 and server 135 perform tasks/functionalities in parallel to provide the computational and processing resources necessary to generate the causal relationship network model described herein.

In some embodiments, each of the server 130, 135, database(s) 140, and database server(s) 145 is connected to the network 105 via a wired connection. Alternatively, one or more of the server 130, 135, database(s) 140, or database server(s) 145 may be connected to the network 105 via a wireless connection. Although not shown, database server(s) 145 can be directly connected to database(s) 140, or servers 130, 135 can be directly connected to the database server(s) 145 and/or database(s) 140. Server 130, 135 comprises one or more computers or processors configured to communicate with client devices 110, 115, 120, 125 via network 105. Server 130, 135 hosts one or more applications or websites accessed by client devices 110, 115, 120, and 125 and/or facilitates access to the content of database(s) 140. Database server(s) 145 comprises one or more computers or processors configured to facilitate access to the content of database(s) 140. Database(s) 140 comprise one or more storage devices for storing data and/or instructions for use by server 130, 135, database server(s) 145, and/or client devices 110, 115, 120, 125. Database(s) 140, servers 130, 135, and/or database server(s) 145 may be located at one or more geographically distributed locations from each other or from client devices 110, 115, 120, 125. Alternatively, database(s) 140 may be included within server 130 or 135, or database server(s) 145.

Figure 2:
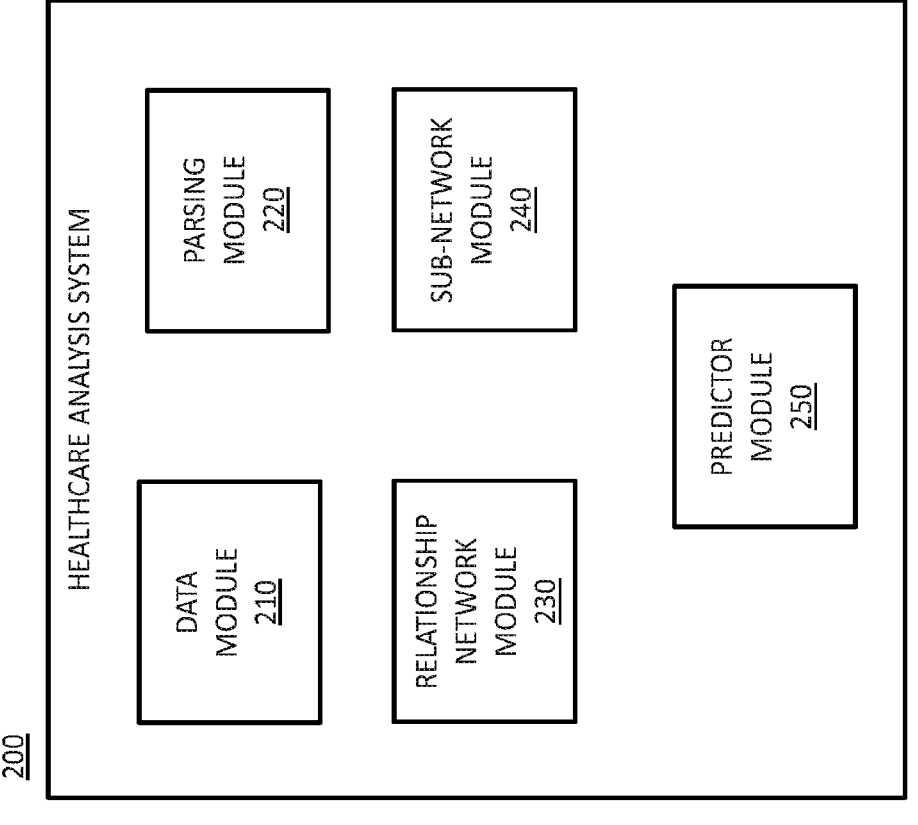
FIG. 2 is a block diagram schematically depicting a healthcare analysis system in terms of modules, according to an embodiment.

FIG. 2 is a block diagram 200 showing a healthcare analysis system implemented in modules according to an example embodiment. In some embodiments, the modules include a data module 210, a parsing module 220, a relationship-network module 230, a sub-network module 240, and a predictor module 250. In an example embodiment, one or more of modules 210, 220, 230, 240, and 250 are be included in server 130 and/or server 135 while other of the modules 210, 220, 230, 240, and 250 are be provided in the client devices 110, 115, 120, 125. For example, the data module 210 may be included in client devices 110, 115, 120, 125, while the parsing module 220, relationship-network module 230, the sub-network module 240 and the predictor module 250 are provided in server 130 or server 135. In another example, the data module 210 may be included in client devices 110, 115, 120, 125, while the parsing module 220 and relationship-network module 230 are provided in server 130, and the sub-network module 240 and the predictor module 250 are provided in server 135. In yet another example, part of functionalities of the relationship-network module 230 may be performed by server 130 and the other part of the functionalities of the relationship-network module 230 may be performed by server 135.

In alternative embodiments, the modules may be implemented in any of client devices 110, 115, 120, 125. The modules may comprise one or more software components, programs, applications, apps or other units of code base or instructions configured to be executed by one or more processors included in client devices 110, 115, 120, 125. In some embodiments, the modules 210, 220, 230, 240, and 250 may be downloaded from a website. In other embodiments, the modules 210, 220, 230, 240, and 250 may be installed from an external hardware component, such as, an external storage component (e.g., USB drive, thumb drive, CD, DVD, etc.).

Although modules 210, 220, 230, 240, and 250 are shown as distinct modules in FIG. 2, it should be understood that modules 210, 220, 230, 240, and 250 may be implemented as fewer or more modules than illustrated. It should be understood that any of modules 210, 220, 230, 240, and 250 may communicate with one or more external components such as databases, servers, database server, or other client devices.

The data module 210 may be a hardware-implemented module configured to receive and manage data. The parsing module 220 may be a hardware-implemented module configured to process, parse, and analyze the received data for a plurality of variables. The relationship-network module 230 may be hardware-implemented module configured to generate a causal relationship network model relating the plurality of variables from the received data using a Bayesian network algorithm. Generating the causal relationship network model may require considerable processor capabilities: therefore, the functionalities of the relationship-network module may be performed by server 130 and server 135 in some embodiments. The sub-network module 240 may be a hardware-implemented module configured to manage a causal relationship network model and determine a sub-network from the causal relationship network model relating to information received from a user. The predictor module 250 may be a hardware-implemented module configured to traverse a sub-network to identify one or more predictors corresponding to the information received from a user.

Figure 3:
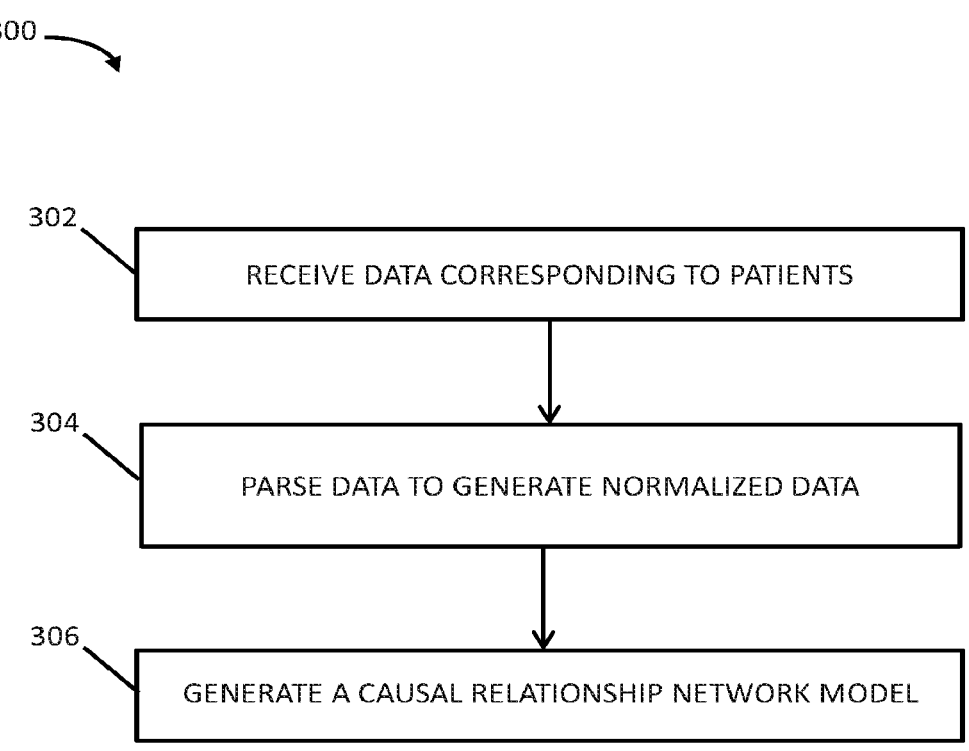
FIG. 3 is a flowchart of a method for healthcare analysis by generation of a relationship network model, according to an embodiment.

FIG. 3 illustrates an example flow diagram 300 of a method for generating a causal relationship network model according to an embodiment. At block 302, data is received corresponding to a plurality of patients. In some embodiments, the data is received by data module 210 (see FIG. 2). In some embodiments, the data includes diagnostic information and/or treatment information for each patient. The data can include information such as any of patient demographics, medical history, patient family medical history, active medication information, inactive past medication information, allergy information, immunization status information, laboratory test results, radiology images, vital sign information, patient weight, billing information, life style information, habits information, insurance claims information, pharmacy information, and the like. Patient demographics may include patient age, patient race, and patient ethnicity. The data can also or alternatively include information from a patient chart, such as notes by a health care professional, observations by a health care professional, administration of drugs and therapies, orders for the administration of drugs and therapies, test results, x-rays, and the like. The data can also or alternatively include patient discharge information, such as a diagnosis code, a treatment code, an insurance charge code, a diagnosis-related group code, an International Classification of Diseases code, and the like. The data module 210 (see FIG. 2) may extract or obtain the data from an entity that manages and makes available various healthcare data, information, and/or statistics. The data can be obtained from a variety of sources, such as publicly available sources, commercial entities that collect data, healthcare providers, and the like. In some embodiments, the data may not be pre-selected or predetermined as being relevant to a plurality of medical conditions or drugs. For an illustrative example of input data, see Example 1 discussed below with respect to FIG. 6.

At block 304, the data received in block 302 is parsed to generate normalized data for a plurality of variables. In some embodiments, the data is parsed by parsing module 220 (see FIG. 2). Normalized data is generated for more than one variable for each patient. Normalization of the data may include reducing the data to its canonical form, and/or organizing the data into a format that is conducive for further use. In some embodiments, parsing the data further includes filtering the data and imputation of the data. Filtering the data may include removal of data points based on criterion like completeness and accuracy of data points. Imputation of the data may include replacing missing data points with appropriate substitute values.

At block 306, a causal relationship-network model is generated based on the generated normalized data for the plurality of variables. In some embodiments, the causal relationship-network model is generated using the relationship-network module 230 (see FIG. 2). In some embodiments, a Bayesian network algorithm is employed to generate the causal relationship network model relating the plurality of variables. In some embodiments, the generated causal relationship network model includes variables relating to a plurality of medical conditions and/or drugs. In some instances, the causal relationship network model is generated using a programmed computing system that includes storage for network model building code, and one or more processors for executing the network model building code. The causal relationship network model may include relationships indicating one or more predictors for each of the plurality medical conditions or drugs. The causal relationship network model may be generated solely on normalized data. In some embodiments, the relationship-network model is an artificial intelligence based network model.

The causal relationship network model may be generated based on as many variables as necessary or appropriate for meaningful data analysis. For example, in some embodiments, the model may be generated based on at least 50 variables. In other embodiments, the model may be generated based on at least 100 variables, on at least 1000 variables, on at least 10,000 variables, on at least 100,000 variables, or on at least 1,000,000 variables. As discussed above, variables correspond to data determined/extracted from the unprocessed/raw input data set. In some embodiments, the variables become nodes in the causal relationship network model.

The causal relationship network model may be generated based on data from as many patients as necessary or appropriate for meaningful data analysis. For example, in some embodiments, the model may be generated based on data from at least 50 patients. In other embodiments, the model may be generated based on data from at least 100 patients, from at least 1000 patients, from at least 10,000 patients, from at least 100,000 patients, or from at least 1,000,000 patients.

The method may include further steps. For example, additional data corresponding to one or more additional patients may be received, at which point, the causal relationship network model may be updated or re-generated based on the additional data.

In some embodiments, a graphical representation of part or all of generated relationship network model may be displayed to a user. In some embodiments, the generated relationship network model is stored for later use.

It should be noted that many different artificial intelligence based platforms or systems may be employed to generate the causal relationships network models using a Bayesian network algorithm. Some example embodiments employ a commercially available system called REFS™ (Reverse Engineering/Forward Simulation) from GNS (Cambridge, MA). AI-Based Systems or Platforms suitable to implement some embodiments employ mathematical algorithms to establish causal relationships among variables based only on an input dataset without taking into consideration prior existing knowledge about any potential, established, and/or verified relationships.

For example, the REFS™ AI-based informatics platform can take normalized input data, and rapidly perform trillions of calculations to determine how data points interact with one another in a system. The REFS™ AI-based informatics platform performs a reverse engineering process aimed at creating an in silico computer-implemented relationship network model, based on the input data, that quantitatively represents relationships between various health conditions and predictors. Further, hypotheses can be developed and rapidly simulated based on the computer-implemented relationship network model in order to obtain predictions, accompanied by associated confidence levels, regarding the hypotheses. Further details regarding an example of generation of the causal relationship model using the REFS platform is provided below.

Figure 4:
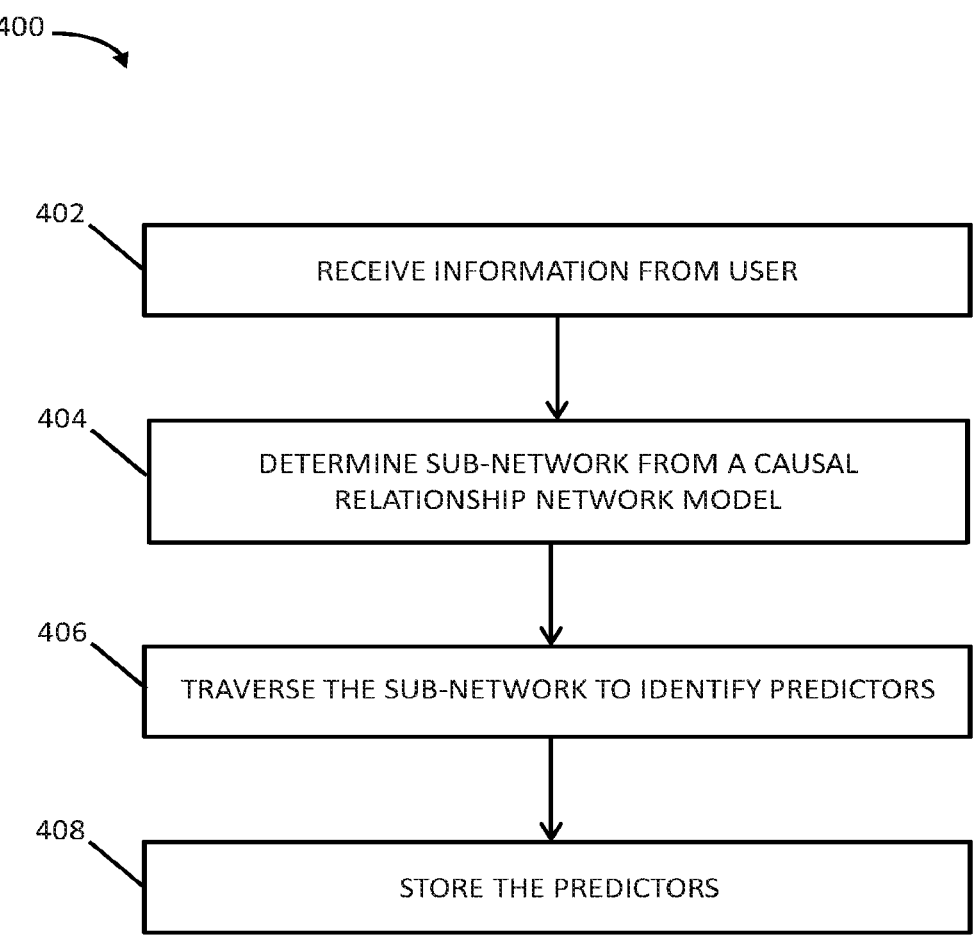
FIG. 4 is a flowchart of a method for using a relationship network model, according to an embodiment.

FIG. 4 illustrates an example flow diagram 400 of a method for using a causal relationship network model according to an embodiment. Method 400 may be implemented in an exemplary system and may be described as a method for using a healthcare analysis system. The method for using a causal relationship network model may also be referred to as a method for interpreting results from a causal relationship network model.

At block 402, information is received from a user. In some embodiments, the information is received by data module 210 (see FIG. 2). In some embodiments, a data module for receiving a collection of data for generation of a relationship network model is different than or separate from a data module that receives information from a user for use of the generated relationship network model.

The information received from the user may include a selection of one or more medical conditions or one or more medical drugs. In some embodiments, the user may be presented with a list of medical conditions and/or medical drugs from which to make a selection.

The information received from the user may be in a form of a query related to one or more medical conditions or one or more medical drugs. In some embodiments, the user may enter text in a search/query field.

In some embodiments, a graphical representation of part or all of the causal relationship network model may be displayed. In some embodiments, the information received from a user may be a selection of one or more nodes displayed in the graphical representation of part or all of the causal relationship network model.

At block 404, a sub-network is determined from a causal relationship network model based on the information received from the user in block 402. In some embodiments, the sub-network is determined by the sub-network module 240. The causal relationship network model from which the sub-network is determined may have been generated from patient data using a Bayesian network algorithm, as discussed above, and may comprise a plurality of variables including variables related to a plurality of medical conditions. One or more variables included in the determined sub-network correspond to the information received from the user. For example, if the received information relates to one or more medical conditions, one or more variables in the sub-network relate to the one or more medical conditions. As another example, if the received information relates to one or more drugs, one or more variables in the sub-network relate to the one or more drugs.

The extent of the sub-network may be determined based on one or more variables associated with the selected one or more medical condition or one or more drugs and the strength of the relationships between the one or more variables and other variables in the causal relationship network model. The sub-network may include one or more variables associated with the medical condition or drug of interest, and a first set of additional variables that each have a first degree relationship with the one or more variables. In some embodiments, the sub-network may further include a second set of additional variables each having a second degree relationship with the one or more variables.

At block 406, the sub-network is traversed to identify predictors. In some embodiments, the sub-network is traversed by the predictor module 250 (see FIG. 2). The predictors are identified as relating to the information received from the user. A predictor is a factor, data point, or node that has a causal relationship to a medical condition or medical drug of interest. For example, renal failure may be a predictor for heart failure. After one or more predictors are identified from the causal relationship network model, the identified predictor can be employed in traditional statistical or regression analysis to determine the significance of the predictor with respect to the medical condition or drug of interest. The one or more predictors for a medical condition of interest may indicate a medical condition co-occurring with the medical condition of interest. The one or more predictors may indicate a drug administered in conjunction with a drug of interest, or indicate an adverse drug interaction. The identified predictor may be a previously unknown or novel predictor for a medical condition or drug. The identified predictor may be newly identified as a predictor for a medical condition or drug. The number of predictors may be less than the number of variables or nodes in the sub-network. At block 408, the identified predictors are stored.

The method above may include further steps. For example, the identified predictors may be displayed in a user interface via a graphical representation of the variables, predictors, and relationships among the variables and predictors. The determined sub-network may be displayed in a user interface.

Generation of a Causal Relationship Network Model

The step of generating a causal relationship network model relating the plurality of variables based on the generated normalized data using a Bayesian network algorithm (block 306 in FIG. 3) is explained in greater detail below with respect to the REFS AI-based informatics system solely for illustrative purposes. However, one of ordinary skill in the art will recognize that other systems employing Bayesian analysis could be employed.

Normalized data for a plurality of variables is input into the REFS system as an input data set. The REFS system creates a library of "network fragments" including the variables (e.g., medical conditions, medical drugs, discharge codes) that drive connections and relationships in a healthcare system. The REFS system selects a subset of the network fragments in the library and constructs an initial trial network from the selected subset. The AI-based system also selects a different subset of the network fragments in the library to construct another initial trial network. Eventually an ensemble of initial trial networks are created (e.g., 1000 networks) from different subsets of network fragments in the library. This process may be termed parallel ensemble sampling. Each trial network in the ensemble is evolved or optimized by adding, subtracting and/or substitution additional network fragments from the library. Further details regarding creation of the network fragment library, creation of trial networks and evolution of the networks is provided below. If additional data is obtained, the additional data may be incorporated into the network fragments in the library and may be incorporated into the ensemble of trial networks through the evolution of each trial network. After completion of the optimization/evolution process, the ensemble of trial networks may be described as the generated relationship network models.

The ensemble of generated relationship network models may be used to simulate the behavior of connections between various medical conditions and/or drugs. The simulation may be used to predict interactions between medical conditions and/or medical drugs, which may be verified using clinical research and experiments. Also, quantitative parameters of relationships in the generated relationship network models may be extracted using the simulation functionality by applying simulated perturbations to each node individually while observing the effects on the other nodes in the generated relationship network models.

The building blocks of REFS incorporates multiple data types, e.g., continuous, discrete, Boolean, from an unlimited number of data modalities. Generating the ensembles of models requires considerable processing power. In some embodiments, the ensembles of models are generated using parallel IBM Blue Gene machines of 30,000+ processors. The resulting network enables high-throughput in silico testing of hypotheses. The network also includes rank order and confidence metrics for predictions that provides verifiable hypotheses.

As noted above, pre-processed data is used to construct a network fragment library. The network fragments define quantitative, continuous relationships among all possible small sets (e.g., 2-3 member sets or 2-4 member sets) of measured variables (input data). The relationships between the variables in a fragment may be linear, logistic, multinomial, dominant or recessive homozygous, etc. The relationship in each fragment is assigned a Bayesian probabilistic score that reflects how likely the candidate relationship is given the input data, and also penalizes the relationship for its mathematical complexity. By scoring all of the possible pairwise and three-way relationships (and in some embodiments also four-way relationships) inferred from the input data, the most likely fragments in the library can be identified (the likely fragments). Quantitative parameters of the relationship are also computed based on the input data and stored for each fragment. Various model types may be used in fragment enumeration including but not limited to linear regression, logistic regression, (Analysis of Variance) ANOVA models, (Analysis of Covariance) ANCOVA models, non-linear/polynomial regression models and even non-parametric regression. The prior assumptions on model parameters may assume Gull distributions or Bayesian Information Criterion (BIC) penalties related to the number of parameters used in the model. In a network inference process, each network in an ensemble of initial trial networks is constructed from a subset of fragments in the fragment library. Each initial trial network in the ensemble of initial trial networks is constructed with a different subset of the fragments from the fragment library.

A model is evolved or optimized by determining the most likely factorization and the most likely parameters given the input data. This may be described as "learning a Bayesian network," or, in other words, given a training set of input data, finding a network that best matches the input data. This is accomplished by using a scoring function that evaluates each network with respect to the input data.

A Bayesian framework is used to determine the likelihood of a factorization given the input data. Bayes Law states that the posterior probability, P(D|M), of a model M, given data D is proportional to the product of the product of the posterior probability of the data given the model assumptions, P(D|M), multiplied by the prior probability of the model, P(M), assuming that the probability of the data, P(D), is constant across models. This is expressed in the following equation:

$$P(M \mid D) = \frac{P(D \mid M) * P(M)}{P(D)}.$$

The posterior probability of the data assuming the model is the integral of the data likelihood over the prior distribution of parameters:

$$P(D|M) = \int P(D|M(\Theta)P(\Theta|M)d\Theta$$

Assuming all models are equally likely (i.e., that P(M) is a constant), the posterior probability of model M given the data D may be factored into the product of integrals over parameters for each local network fragment $M_i$ as follows:

$$P(M \mid D) = \prod_{i=1}^{n} \int P_i(X_i \mid Y_{j1}, \dots, Y_{jK_i}; \Theta_i).$$

Note that in the equation above, a leading constant term has been omitted. In some embodiments, a Bayesian Information Criterion (BIC), which takes a negative logarithm of the posterior probability of the model P(D|M) may be used to "Score" each model as follows:

$$S_{tot}(M) = -\log P(M \mid D) = \sum_{i=1}^{n} S(M_i),$$

where the total score $S_{tot}$ for a model M is a sum of the local scores Si for each local network fragment. The BIC further gives an expression for determining a score each individual network fragment:

$$S(M_i) \approx S_{BIC}(M_i) = S_{MLE}(M_i) + \frac{\kappa(M_i)}{2}\log N$$

where $\kappa(M_i)$ is the number of fitting parameter in model $M_i$ and N is the number of samples (data points). $S_{MLE}(M_i)$ is the negative logarithm of the likelihood function for a network fragment, which may be calculated from the functional relationships used for each network fragment. For a BIC score, the lower the score, the more likely a model fits the input data.

The ensemble of trial networks is globally optimized, which may be described as optimizing or evolving the networks. For example, the trial networks may be evolved and optimized according to a Metropolis Monte Carlo Sampling algorithm. Simulated annealing may be used to optimize or evolve each trial network in the ensemble through local transformations. In an example simulated annealing processes, each trial network is changed by adding a network fragment from the library, by deleting a network fragment from the trial network, by substituting a network fragment or by otherwise changing network topology, and then a new score for the network is calculated. Generally speaking, if the score improves, the change is kept and if the score worsens the change is rejected. A "temperature" parameter allows some local changes which worsen the score to be kept, which aids the optimization process in avoiding some local minima. The "temperature" parameter is decreased over time to allow the optimization/evolution process to converge.

All or part of the network inference process may be conducted in parallel for the trial different networks. Each network may be optimized in parallel on a separate processor and/or on a separate computing device. In some embodiments, the optimization process may be conducted on a supercomputer incorporating hundreds to thousands of processors which operate in parallel. Information may be shared among the optimization processes conducted on parallel processors. In some embodiments, the optimization process may be conducted on one or more quantum computers, which have the potential to perform certain calculations significantly faster than a silicon-based computer.

The optimization process may include a network filter that drops any networks from the ensemble that fail to meet a threshold standard for overall score. The dropped network may be replaced by a new initial network. Further any networks that are not "scale free" may be dropped from the ensemble. After the ensemble of networks has been optimized or evolved, the result may be termed an ensemble of generated relationship network models, which may be collectively referred to as the generated consensus network.

Simulation may be used to extract quantitative parameter information regarding each relationship in the generated relationship network models. For example, the simulation for quantitative information extraction may involve perturbing (increasing or decreasing) each node in the network by ten-fold and calculating the posterior distributions for the other nodes in the models. The endpoints are compared by t-test with the assumption of 100 samples per group and the 0.01 significance cut-off. The t-test statistic is the median of 100 t-tests. Through use of this simulation technique, an area under the curve (AUC) representing the strength of prediction and fold change representing the in silico magnitude of a node driving an end point are generated for each relationship in the ensemble of networks.

A relationship quantification module of a local computer system may be employed to direct the AI-based system to perform the perturbations and to extract the AUC information and fold information. The extracted quantitative information may include fold change and AUC for each edge connecting a parent note to a child node. In some embodiments, a custom-built R program may be used to extract the quantitative information.

In some embodiments, the ensemble of generated relationship network models can be used through simulation to predict responses to changes in conditions, which may be later verified through clinical research and experiments.

The output of the AI-based system may be quantitative relationship parameters and/or other simulation predictions. Some exemplary embodiments incorporate methods that can be performed using the Berg Interrogative Biology™ Informatics Suite, which is a tool for understanding a wide variety of biological processes, such as disease pathophysiology, and the key molecular drivers underlying such biological processes, including factors that enable a disease process. Some exemplary embodiments employ the Berg Interrogative Biology™ Informatics Suite to gain novel insights into disease interactions with respect to other diseases, medical drugs, biological processes, and the like. Some exemplary embodiments include systems that may incorporate at least a portion of, or all of, the Berg Interrogative Biology™ Informatics Suite.

EXAMPLES

Example 1—Relationship Network Model Generated from CMS Data: Sub-Network of Heart Failure & Shock and Renal Failure Mathematical and statistical learning tools developed in Artificial Intelligence (AI) are well adapted to decipher complex interaction patterns in Big Data. The Berg Interrogative Biology™ Informatics Suite is a computational workflow for integration of varied data modalities and inference of causal effects in a purely data-driven manner using Bayesian Networks (BN). The present example relates to the use of BNs in healthcare Big Data analytics that has a significant impact on enhancing patient care and improving healthcare and hospital efficiency.

Low-resolution, publicly available data was used to make novel discoveries that directly informed care and lead to novel hypotheses using a generated causal relationship network model. A data relationship network of diagnosis codes was generated based on publicly available billing data from Centers for Medicare & Medicaid Services (CMS).

Figure 5:
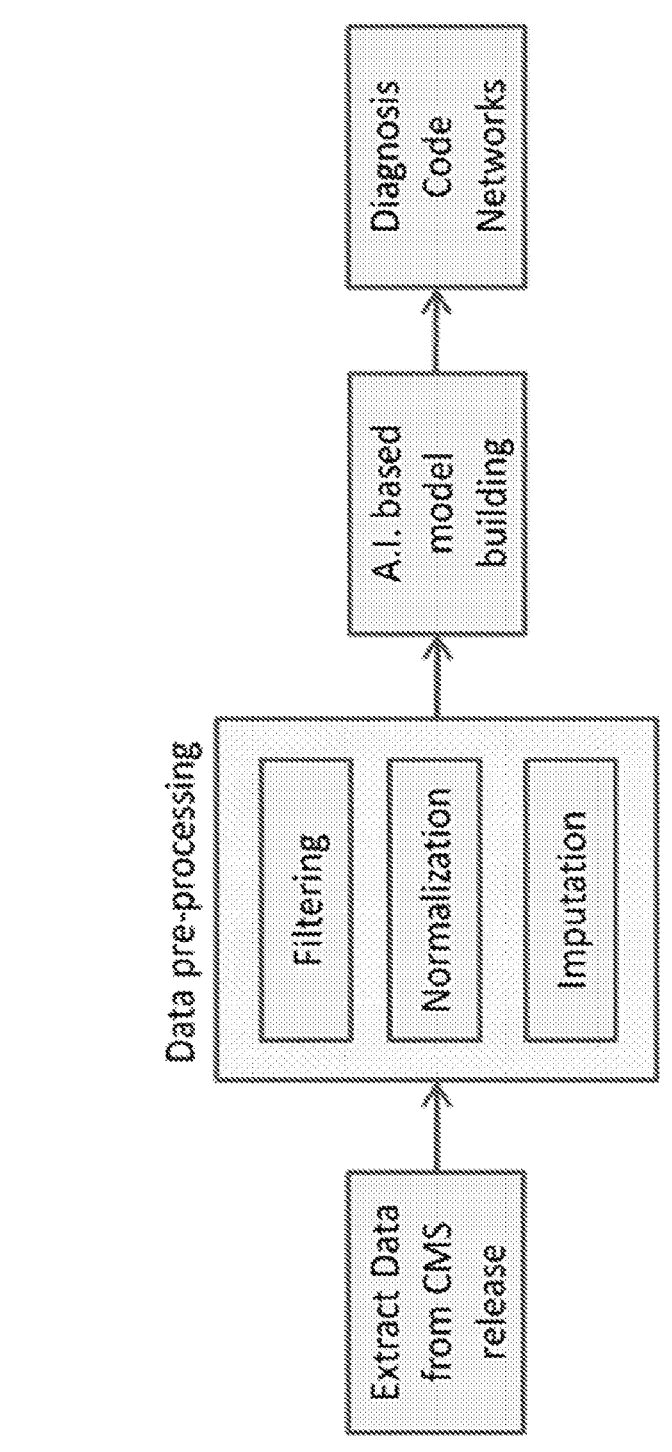
FIG. 5 is a flowchart of a method for healthcare analysis in Example 1.

As schematically depicted in method 500 of FIG. 5, data was extracted from a CMS release. The data was preprocessed by filtering, normalization, and imputation. A.I. based model building was used to generate a model from the pre-processed data resulting in relationship networks in the form of diagnosis code networks.

The collection of data was obtained from a CMS data release. CMS releases (i.e., makes publicly available on its website) data relating to patient care, insurance information, diagnosis codes, discharges codes, and charge codes for various procedures for healthcare providers. FIG. 6 shows a sample of a portion of the CMS data for a single medical institution. In this Example, the data obtained included multiple healthcare providers and the top 100 diagnosis codes for the year 2011.

The Berg Interrogative Biology™ Informatics Suite was used for data pre-processing and model building. The collected data was processed so that columns containing information about the Diagnosis Related Group (DRG) codes and total number of discharges was extracted from the dataset. Discharge count information was organized as a matrix of DRG codes versus hospitals. DRG codes that were missing in more than 70% of hospitals were removed from further analysis. Hospitals with missing information for more than 25 DRG codes were filtered from the dataset. After filtering, the dataset contained 100 DRG codes and 1618 hospitals. Median polish normalization was performed on this data matrix, and missing data was imputed with 'zero procedures.' Causal relationship network models were built using REFS technology. The connections in the resulting relationship networks were filtered with an area-under-the-curve (AUC) cut-off of 0.65. The resulting network was visualized using suitable graphical environment/interface software, specifically Cytoscape, a software environment for integrated models of biomolecular interaction networks from the Cytoscape Consortium. Within the Cytoscape environment, networks are visualized as "nodes" connected by "edges", each of which graphically depicts a relationship between the two nodes connected by the edge.

Figure 7:
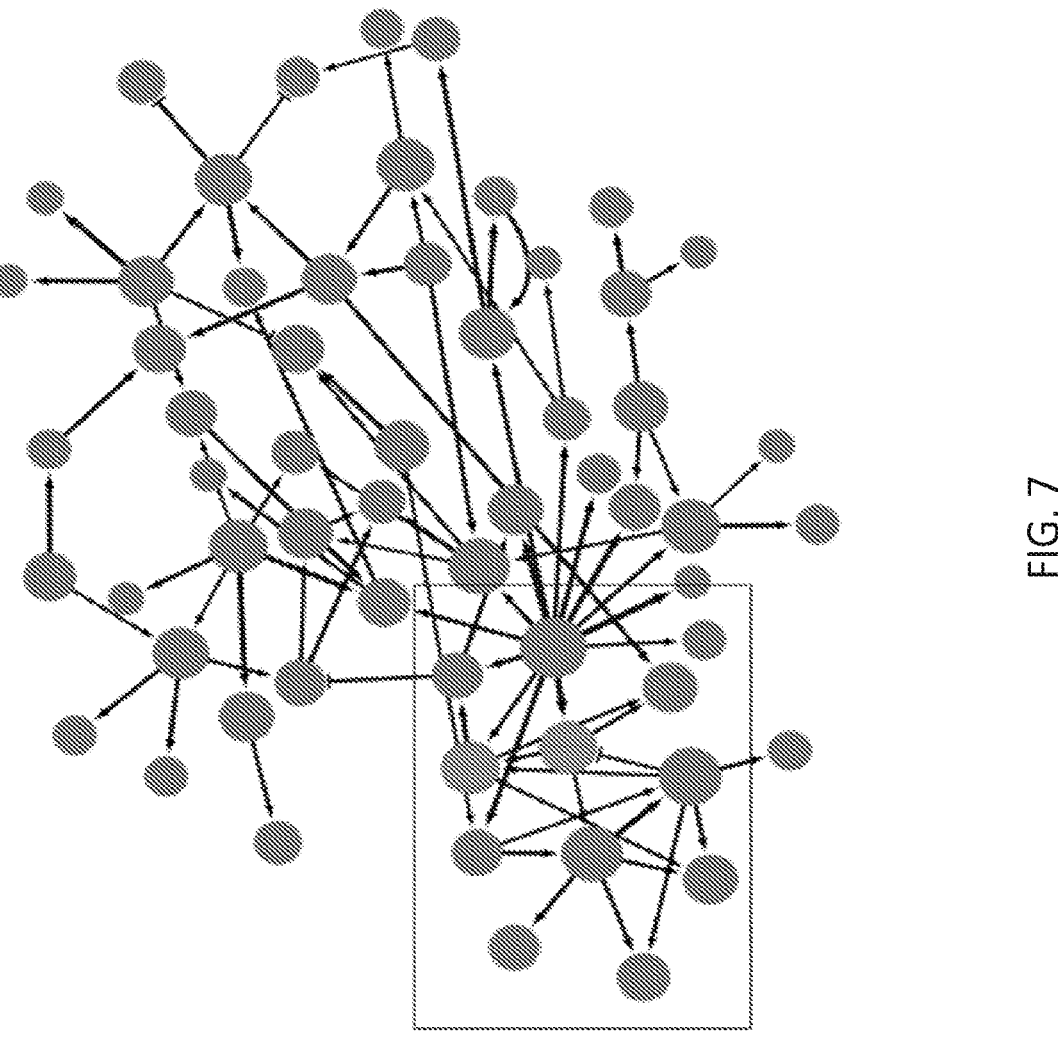
FIG. 7 schematically depicts a relationship network model generated in Example 1.

A schematic graphical depiction of the generated relationship network based on DRG codes is shown in FIG. 7. This particular relationship network contained 60 diagnoses and 88 connections/relationships linking them. Each node in the network represented the number of discharges for a particular diagnosis, and the edges (e.g., connections between nodes) represented interactions between the numbers of discharges associated with various diagnoses. In FIG. 7, the size of the node corresponds to the number of discharge codes for the particular diagnosis. Interpretation of the edges and the connections in the network depended on specific diagnoses involved. For example, when the source node is diabetes and the target node is hypertension, the connection represents co-morbidities. When the source node is diabetes and the target node is neuropathy, the connection represents complications from the disease. In this manner, the relationship network represented interactions between a number of DRG codes.

A sub-network was selected to obtain relevant information from the generated relationship network. A sub-network (shown in FIG. 8) centered on 'heart failure & shock' and 'renal failure' was determined from the causal relationship network model shown in FIG. 7. In this example, 'Heart failure & shock' and 'renal failure' were selected due to their prominence in the death index compiled by the Center for Disease Control and Prevention (CDC). According to the CDC report, heart disease was the top cause of death in 2011. Some kidney related conditions were ranked 9, 12, and 13; however, all kidney related conditions combined play a major role as a cause of death.

Figure 8:
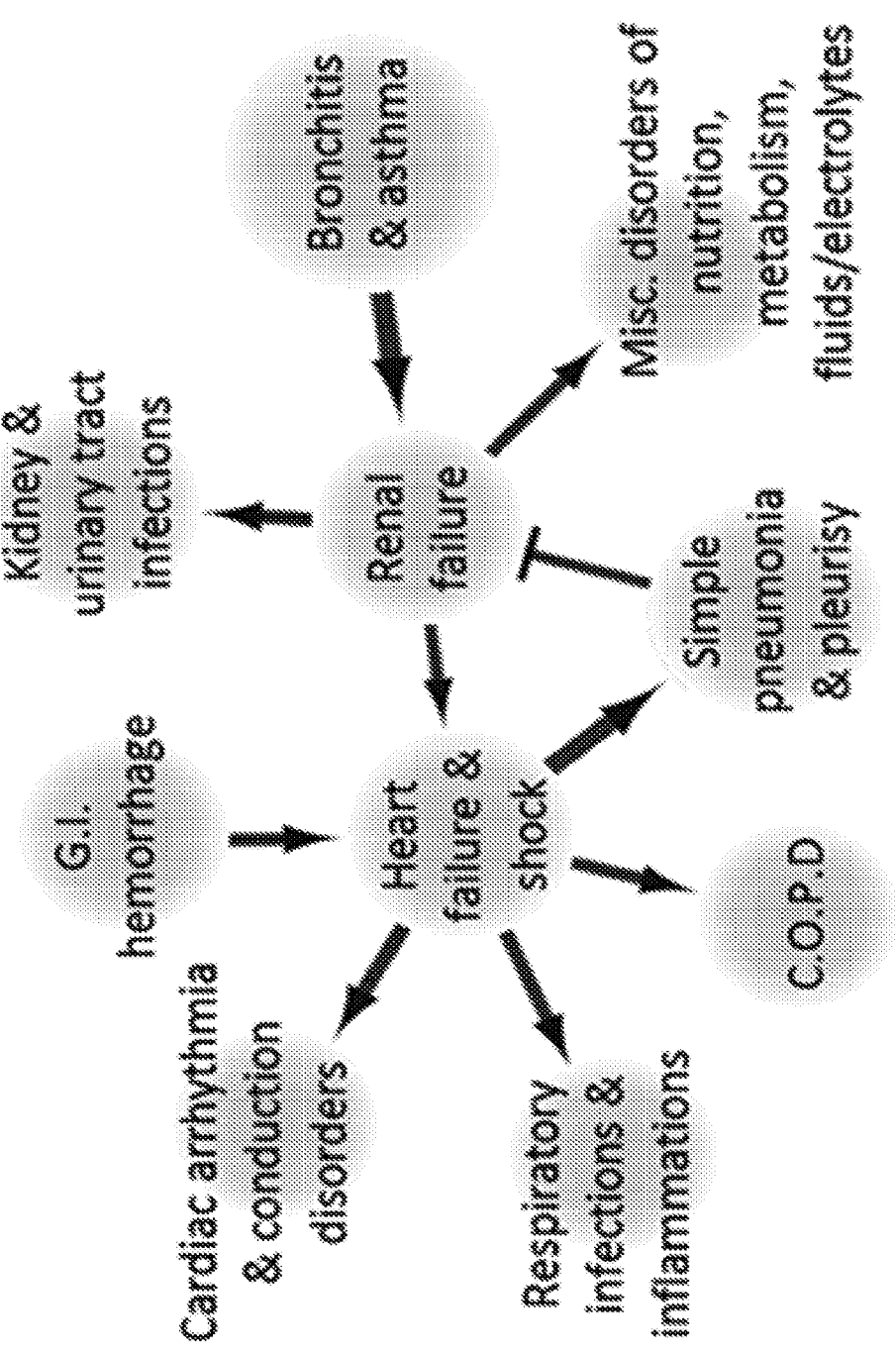
FIG. 8 schematically depicts a sub-network of the relationship network model of FIG. 7 that is focused on heart failure & shock and renal failure.

In the graphical depiction of the sub-network in FIG. 8, connections in the form of arrows indicate that the number of diagnoses in the first condition and the number of diagnoses in the second condition are positively correlated. Clinically, connections can be interpreted in different ways depending on the conditions involved (e.g., the arrow from heart failure & shock to simple pneumonia & pleurisy indicates that heart failure & shock leads to or is followed by simple pneumonia & pleurisy in a statistically significant proportion of patients). Each connection between notes, which is shown as a line, may also be described as an edge between the nodes. The width of the line (also described as the "weight" of the line) forming the connection between nodes provides a graphical indication of the strength of the relationship between the nodes. For example, the arrow from heart failure & shock to simple pneumonia & pleurisy is wider than the arrow connecting heart failure & shock to respiratory infections & inflammations. This means that the model predicted that the relationship between heart failure & shock and simple pneumonia & pleurisy is stronger than the relationship between heart failure & shock and respiratory infection & inflammations.

Connections in the heart failure sub-network and in the renal failure sub-network served as validation that the connections appearing in the relationship network model were reliable as discussed below.

Figure 9B:
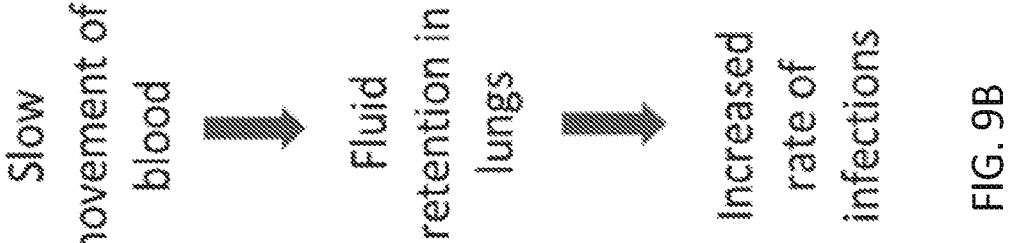
FIG. 9B schematically depicts how heart failure & shock may lead to simple pneumonia & pleurisy and respiratory infections & inflammations.
Figure 9A:
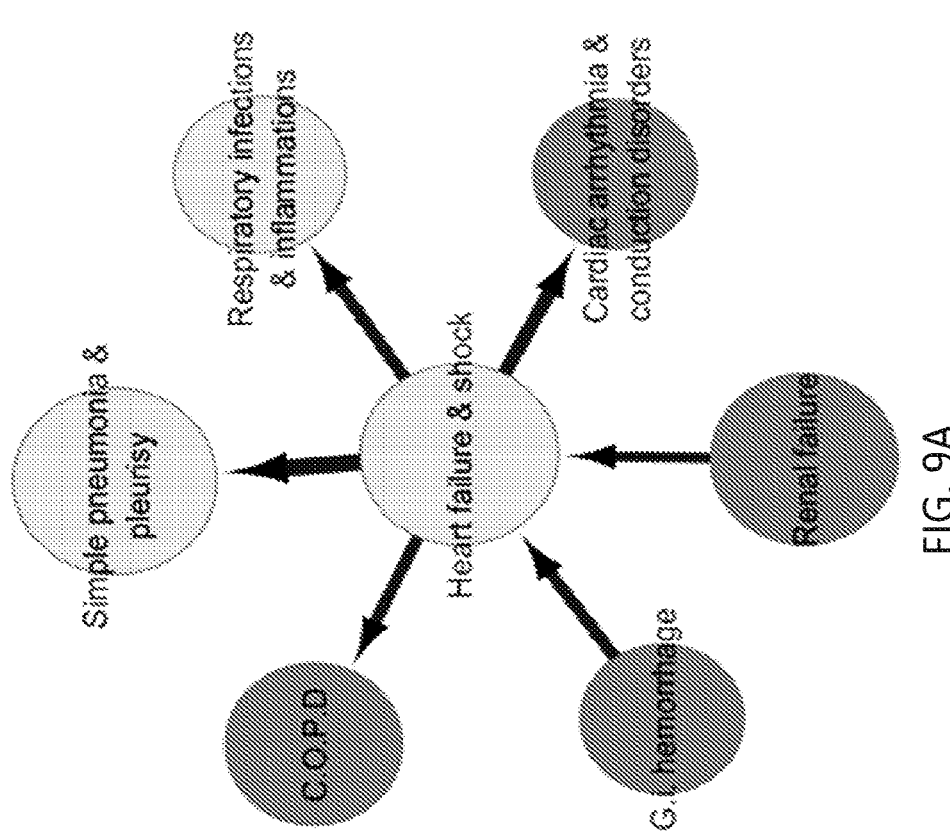
FIG. 9A schematically depicts a sub-network of the relationship network model of FIG. 7 focusing on heart failure & shock and highlighting a connection between heart failure & shock and simple pneumonia & pleurisy, and a connection between heart failure & shock and respiratory infections.

Heart failure is caused by conditions that reduce the ability of the heart to pump blood efficiently. These conditions include congenital heart defects, arrhythmias, coronary artery disease that narrows arteries over time, and high blood pressure that could make the heart too weak or stiff to pump blood effectively. Relationships between heart failure and other conditions, which are reflected in connections between heart failure and other nodes in the sub-network are discussed below:

Respiratory infections and inflammations simple pneumonia and pleurisy: It is well-known that heart failure causes blood to move through the body at a slower pace and causes the kidneys to retain fluids. Fluid retention starts in the lower part of the body but progresses to the lungs causing pneumonia. Fluid buildup in the lungs leads to increased rate of respiratory infections and respiratory infections. The relationship network model predicted that a diagnosis of heart failure & shock leads to or is followed by a diagnosis of simple pneumonia and pleurisy in a statistically significant proportion of patients, as indicated by the arrow from heart failure & shock to simple pneumonia and pleurisy in FIG. 9A. The relationship network model predicted that a diagnosis of heart failure & shock leads to or is followed by a diagnosis of respiratory infections & inflammations in a statistically significant proportion of patients, as indicated by the arrow from heart failure & shock to respiratory infections & inflammations in FIG. 9A. FIG. 9B graphically depicts a path by which heart failure and shock can lead to simple pneumonia and pleurisy and respiratory infections and inflammations.

Figure 10B:
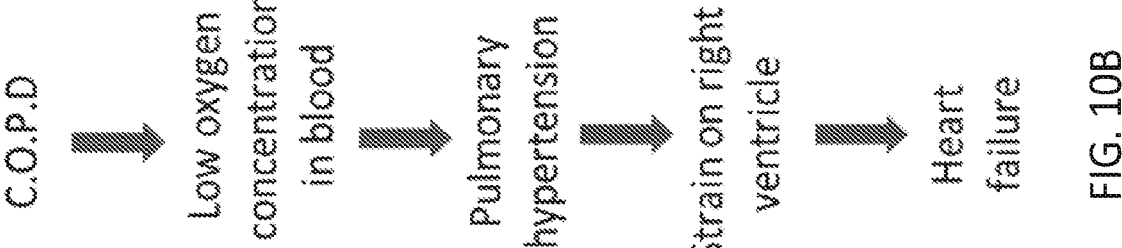
FIG. 10B schematically depicts how COPD may lead to heart failure.
Figure 10A:
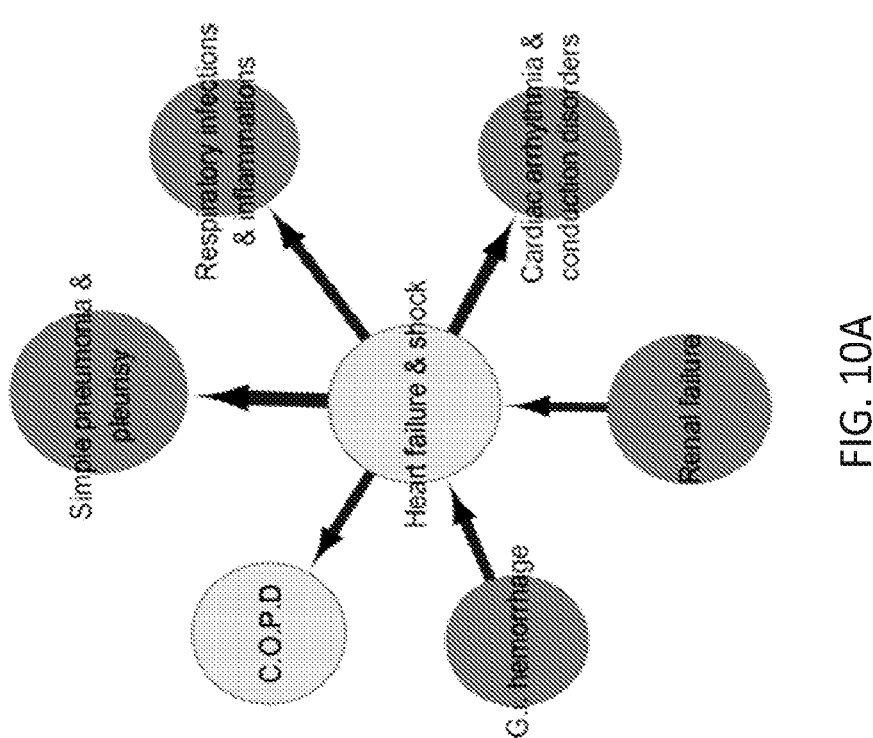
FIG. 10A schematically depicts the heart failure & shock sub-network of FIG. 9A highlighting a connection between heart failure & shock and COPD.

Chronic obstructive pulmonary disease (COPD): COPD causes pulmonary hypertension when the lungs try to compensate for low oxygen concentration in blood by increasing the blood pressure inside the lungs. Increase in blood pressure inside the lungs results in pulmonary hypertension which strains the right ventricle and causes the heart to fail. Therefore, diagnosis of heart failure can lead to diagnosis of previously undiagnosed COPD. Thus, the increase in number of heart failure diagnosis will increase the number of diagnosis for COPD. The relationship network model predicted that an increase in number of diagnoses of heart failure & shock leads to an increase in number of diagnoses of COPD as indicated by the arrow from heart failure & shock to COPD in FIG. 10A. This could be directly interpreted as heart failure & shock causing COPD in statistically significant number of patients. However, FIG. 10B graphically depicts a path by which COPD leads to heart failure & shock, not heart failure & shock leading to COPD. This apparent reverse in timing between the model predication and the known relationship between heart failure and COPD is likely due to previously undiagnosed COPD being diagnosed after heart failure. A clinician may find COPD only after heart failure leads to a search for a cause. Thus, although the COPD is present before the heart failure, the COPD is not diagnosed until after the diagnosis of heart failure.

Figure 11:
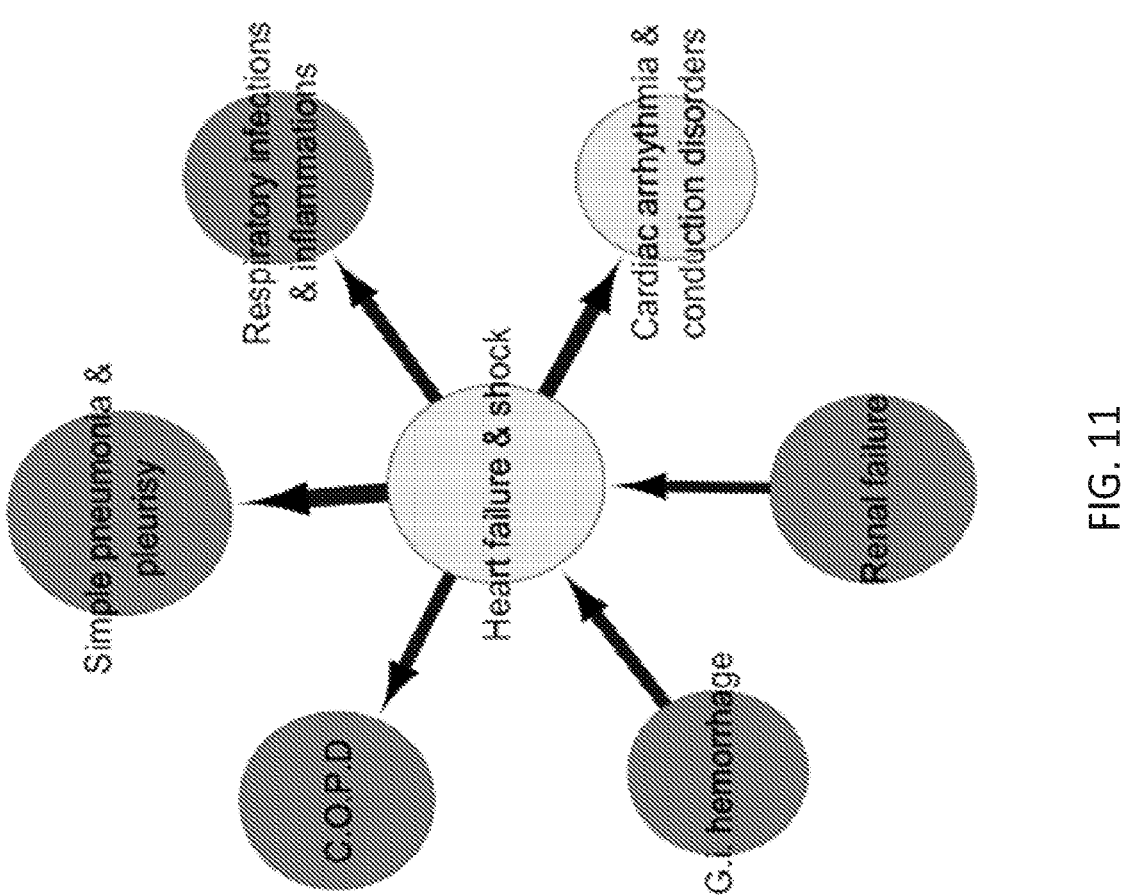
FIG. 11 schematically depicts the heart failure & shock sub-network highlighting a connection between heart failure & shock and cardiac arrhythmia & conduction disorders.

Cardiac arrhythmia and conduction disorders: Cardiac arrhythmia and conduction disorders can directly cause heart failure. Diagnosis of heart failure can leads to diagnosis of these causal conditions. Therefore increase in number of heart failure diagnoses will increase the number of diagnoses of cardiac arrhythmias and conduction disorders. The relationship network model predicted that an increase in the number of diagnoses of heart failure and shock leads to or is followed by an increase in the number of diagnoses of cardiac arrhythmia & conduction disorders in a statistically significant proportion of patients, as indicated by the arrow from heart failure and shock to cardiac arrhythmia & conduction disorders in FIG. 11.

Figure 12B:
FIG. 12B schematically depicts how G.I. hemorrhage can lead to heart failure.
Figure 12A:
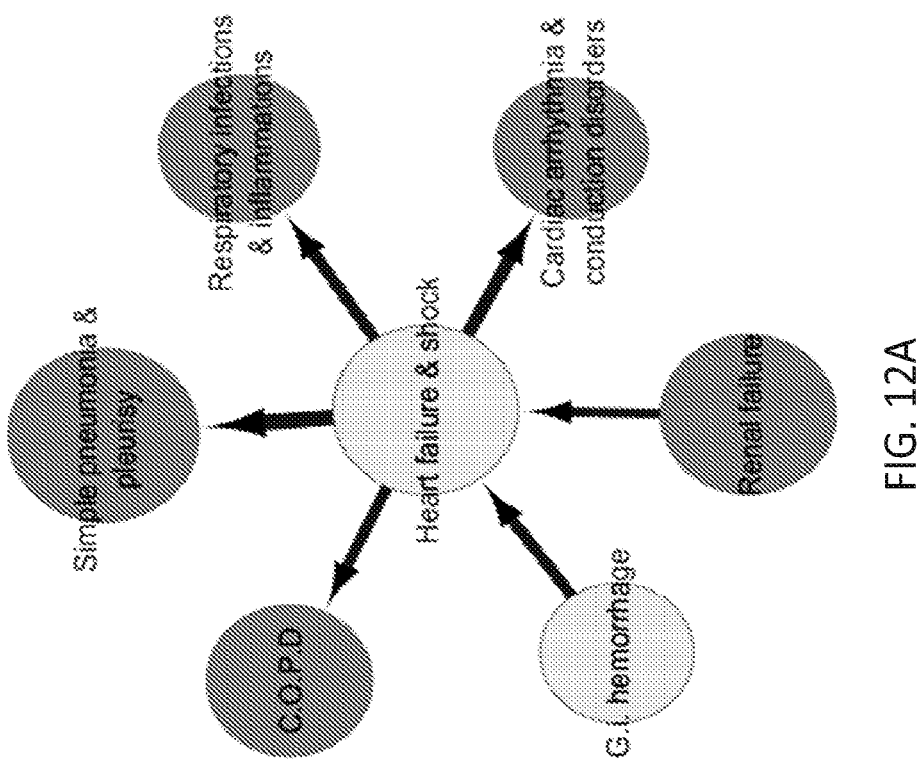
FIG. 12A schematically depicts the heart failure & shock sub-network highlighting a connection between G.I. hemorrhage and heart failure & shock.

Gastrointestinal (G.I.) hemorrhage: Heart failure can be a result of hypovolemic shock. Hypovolemic shock occurs due to rapid loss of volume of circulating blood. The most frequent causes of hemorrhagic shock (precursor to hypovolemic shock) are trauma, G.I hemorrhage and organ injury. The relationship network model predicted that a diagnosis of G.I. hemorrhage leads to or is followed by a diagnosis of heart failure & shock in a statistically significant proportion of patients, as indicated by the arrow from G.I. hemorrhage to heart failure and shock in FIG. 12A. FIG. 12B graphically depicts the path by which G.I. hemorrhage leads to heart failure.

Figure 13:
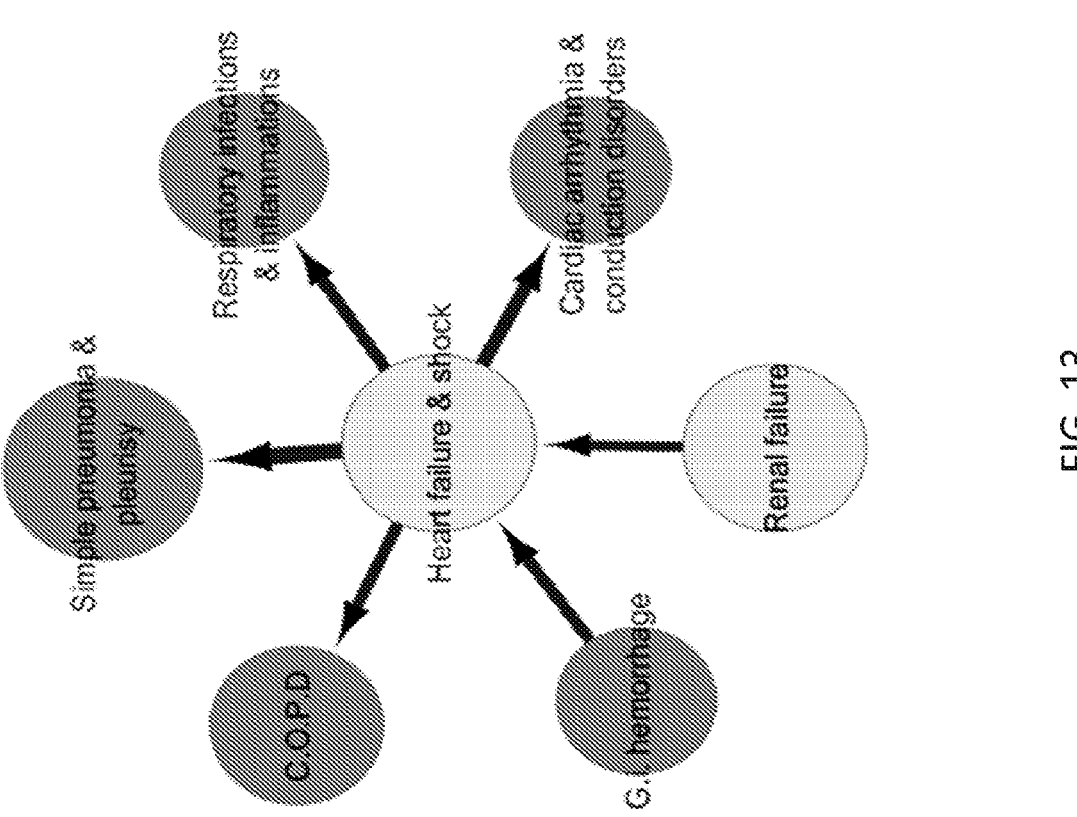
FIG. 13 schematically depicts the heart failure & shock sub-network highlighting a connection between renal failure and heart failure & shock.

Renal failure: The link between anemia, cardiac problems and renal disease is well-known, and the challenges of treating patients with cardio-renal insufficiencies have been documented. About one-fourth of the patients with renal disease have congestive heart problems. As renal disease worsens, the fraction of patients with heart disease increases to about 65-70%. Large studies have shown that worsening kidney disease is associated with higher mortality and hospitalization rates in patients with previous diagnosis of heart failure. Therefore, this connection is already well-known. The relationship network model predicted that a diagnosis of renal failure leads to or is followed by a diagnosis of heart failure and shock in a statistically significant proportion of patients, as indicated by the arrow from renal failure to heart failure & shock in FIG. 13.

Figure 14A:
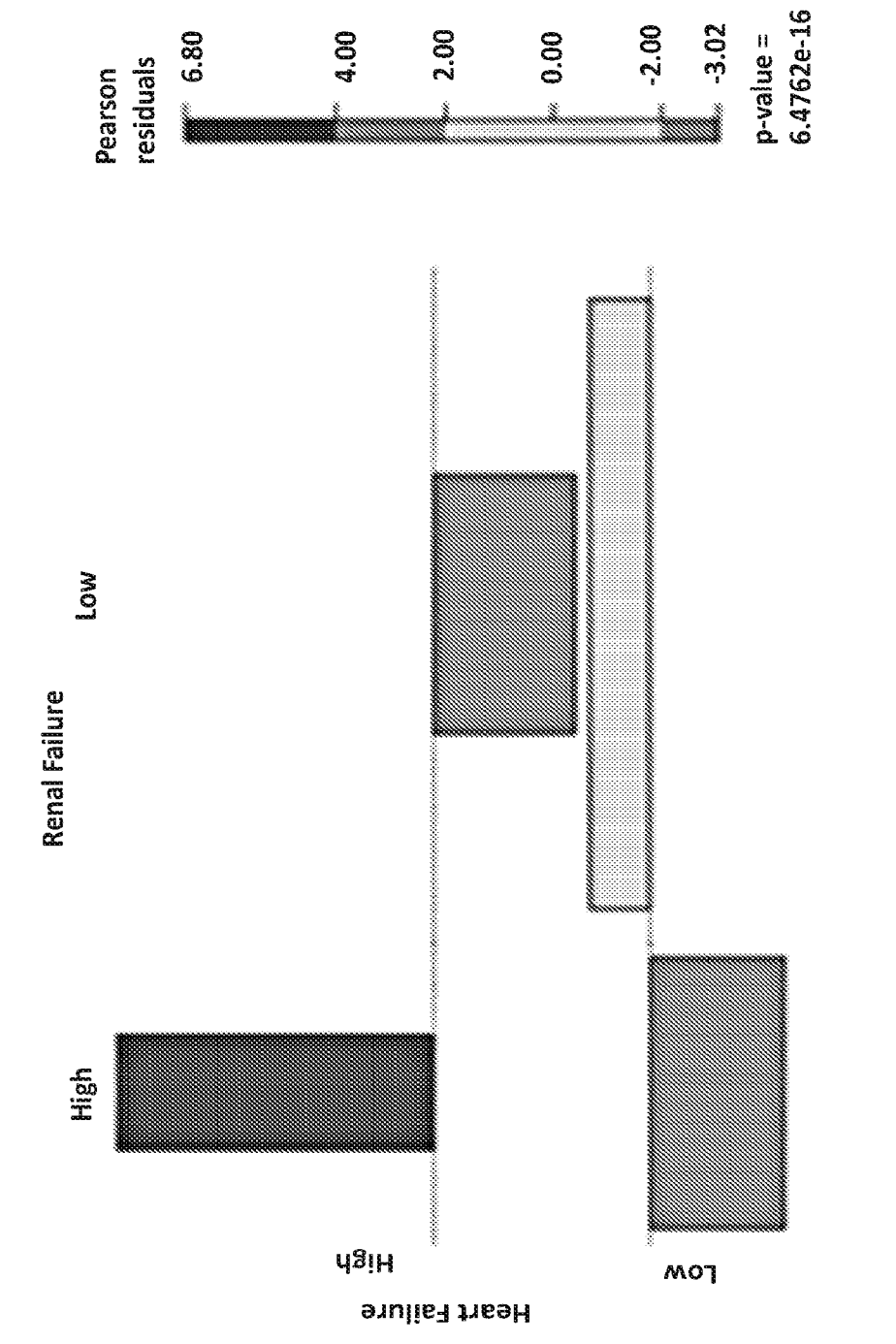
FIG. 14A is an association plot of heart failure & shock with renal failure generated from the relationship network model in Example 1.
Figure 14B:
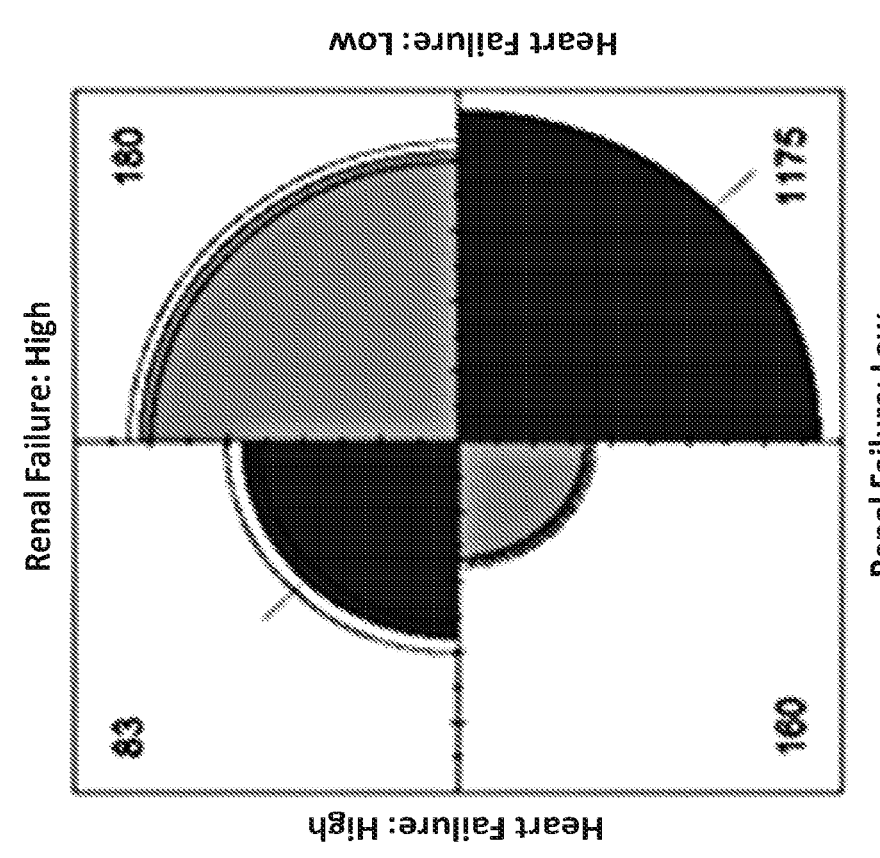
FIG. 14B is a fourfold plot of heart failure & shock with renal failure generated from the relationship network model in Example 1.

FIGS. 14A and 14B provide further details regarding the relationship network model's prediction for the strength of the relationship between heart failure & shock and renal failure. FIG. 14A is an association plot of heart failure and renal failure derived from data used for building the relationship network model. An association plot, which can be represented as a 2×2 table, shows deviation of the observed frequencies from the expected frequencies for variables in a data set. Pearson residuals indicate the distance between the expected and observed frequencies, and therefore, allow for identification of categories that drive deviation from expected values. In the association plot of FIG. 14A, the width of the each rectangle indicates the number of data points and the height and color are representative of the Pearson residual. In this case, the expected values were calculated based on the null hypothesis that heart failure and renal failure are independently distributed. If this were true, the plot would be primarily light grey indicating Pearson residuals near zero (i.e., less than 2 and greater than −2). Instead, medium grey sections representing Pearson residuals less than −2 and a dark grey section representing a Pearson residual greater than 2 were observed indicating that heart failure and renal failure are not independent, hence deviating from the null hypothesis. The biggest component driving change, as indicated by the Pearson residual, was in the high categories for both renal failure and heart failure. In summary, in this case, the association plot of FIG. 14A indicated an interaction between heart failure and renal failure. This interaction is primarily driven by patients that have both renal failure and heart failure.

FIG. 14B is a fourfold plot of heart failure and renal failure, which was derived from data used for building the relationship network model. A four-fold plot is another representation of the departure from independence between categories of interest. In a four-fold plot. The numbers within each square indicate the number of data points in that category. FIG. 14B shows the effect of renal failure on heart failure. Based on comparing the size of quarter circles, the left half of the plot indicates that as compared to low renal failure rates, high renal failure rates have a stronger effect on high heart failure rates. The right half of the plot indicates smaller differences in the effect of high or low renal failure on low heart failure rate. In summary, this plot reinforces interaction between conditions of interest: heart failure and renal failure. The relative risk of heart failure with renal failure was calculated to be 2.57 based on the relationship network model.

Figure 15A:
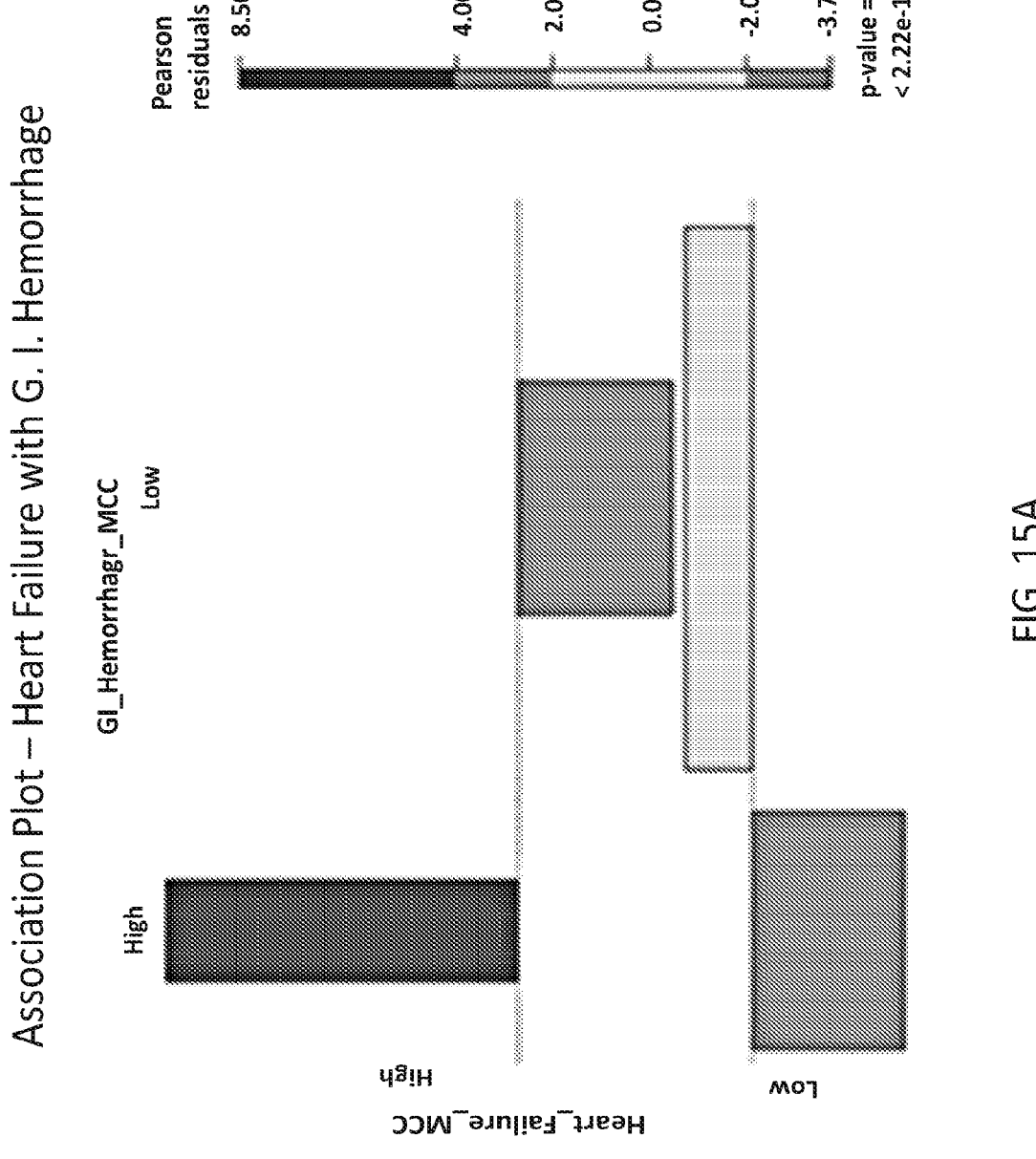
FIG. 15A is an association plot of heart failure & shock with G.I. hemorrhage generated from the relationship network model in Example 1.
Figure 15B:
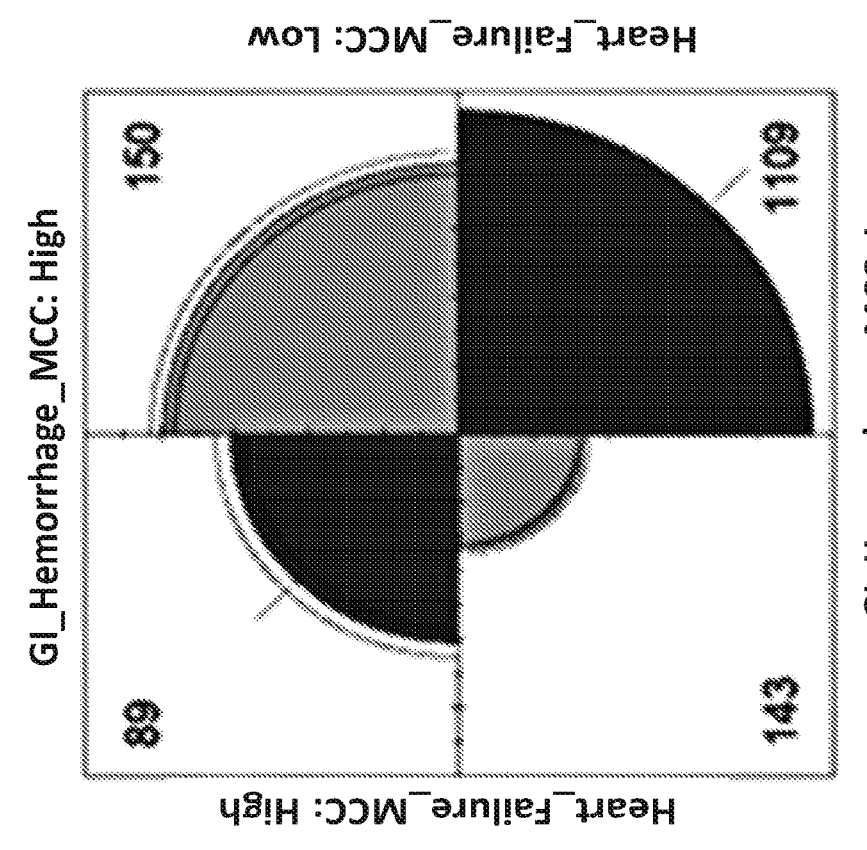
FIG. 15B is a fourfold plot of heart failure & shock with G.I. hemorrhage generated from the relationship network model in Example 1.

FIGS. 15A and 15B provide further details regarding the relationship network model's prediction for the strength of the relationship between heart failure & shock and G.I. hemorrhage. FIG. 15A is an association plot of heart failure and G.I. hemorrhage. In this plot, the dark grey rectangle, representing a Pearson residual greater than 4.0 and the medium grey rectangles, representing Pearson residuals less than −2, indicate that G.I. hemorrhage and heart failure are not independent. In particular, the dark grey rectangle shows that high rates of both conditions have the strongest interactions. FIG. 15B is a fourfold plot of heart failure and G.I. hemorrhage. This plot, indicates that high rates of heart failure are strongly associated with high rates of G.I. Hemorrhage. As shown, the relative risk of heart failure with G.I. hemorrhage was calculated to be 3.22.

The relationship network model was generated based only on DRG and discharge codes without any assumptions or other information regarding the relationships between heart disease & shock and the various conditions (i.e., simple pneumonia and pleurisy, respiratory infections and inflammations, COPD, cardiac arrhythmia & conduction disorders, G.I. hemorrhage, and renal failure). Nevertheless, sub-network of the generated relationship network model that centered on heart failure and shock reflected the current knowledge in the medical field regarding the relationships between heart failure & shock and the other conditions, which supports the validity of the relationship network model.

Figure 16:
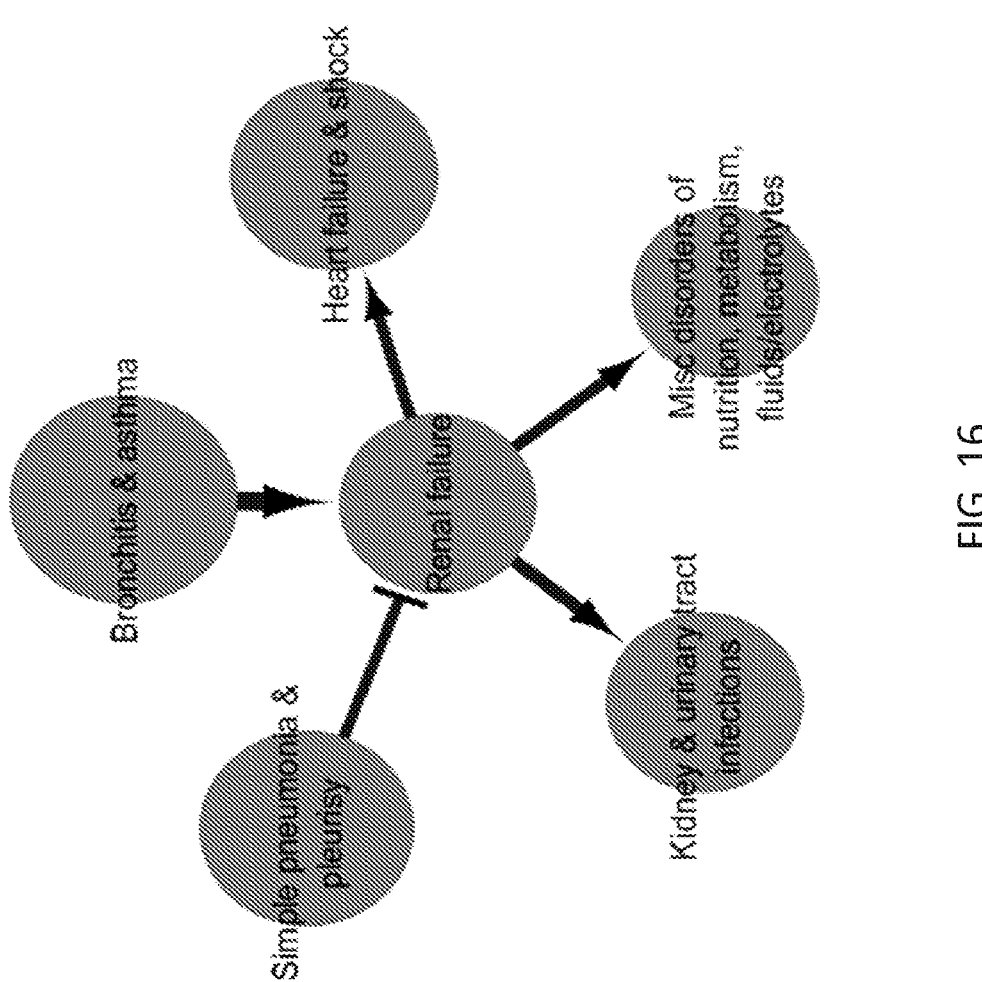
FIG. 16 schematically depicts a second portion of the sub-network of FIG. 8 focusing on renal failure.

The diagnoses code corresponding to renal failure in this analysis encompassed chronic/acute kidney failure and other renal disorders. Renal failure/insufficiency refers to reduction in the kidney's ability to remove waste products from blood. More than 10% of adults 20 years or older have CKD and the cost of treating CKD is very high because of costs linked to co-morbidities and quality of life factors. One study shows that the cost for treating end stage renal disease (ESRD) is continually increasing and Medicare costs for this condition reached 30 billion dollars in 2009. A sub-network centered on renal failure, is schematically depicted in FIG. 16. The connections with renal failure in the sub-network are explored below:

Kidney and urinary tract infections: The relationship network model predicted a statistically significant relationship between renal failure and kidney and urinary tract infections, as shown by the arrow from renal failure to kidney & urinary tract infections in FIG. 16. It is known that untreated urinary tract and kidney infections can lead to kidney failure. Though the reversal in directionality remains as yet unexplained, linkage between the conditions is represented in the relationship network model. Therefore, it is not surprising that this connection between identified.

Disorders of nutrition, metabolism, and fluids electrolytes: Kidneys play an important role in maintaining the fluid and electrolyte balance. Therefore it is possible that a diagnosis of renal failure would lead to follow up tests and diagnosis of nutrition, metabolism, fluid and electrolyte balance problems. The relationship network model predicted that a diagnosis of renal failure leads to a diagnosis of disorders of nutrition, metabolism, and fluids/electrolytes in a statistically significant proportion of patients, as shown by the arrow from renal failure to disorders of nutrition, metabolism, and fluids/electrolytes as shown in FIG. 16.

Simple pneumonia and pleurisy: It is established that chronic kidney disease increases susceptibility to infections, and pneumonia has been documented as an infectious complication of kidney disease. The relationship network model predicted a statistically significant relationship between renal failure and simple pneumonia & pleurisy, as shown by connection between renal failure and simple pneumonia & pleurisy in FIG. 16. In the graphical depiction of the sub-network in FIG. 8, the connection in the form of a T-shape indicates that the number of diagnoses in the first condition and the number of diagnoses in the second condition are negatively correlated. Specifically, that the number of diagnoses of simple pneumonia & pleurisy and the number of diagnoses of renal failure are negative correlated.

With respect to the renal failure centered sub-network, all but one connection in the selected sub-network (specifically, all but the connection between bronchitis & asthma and renal failure) are supported by current knowledge in the medical field. This serves as further validation that results from the generated relationship network model are dependable, and that novel predictions of interactions are worthy of further investigation.

Figure 17A:
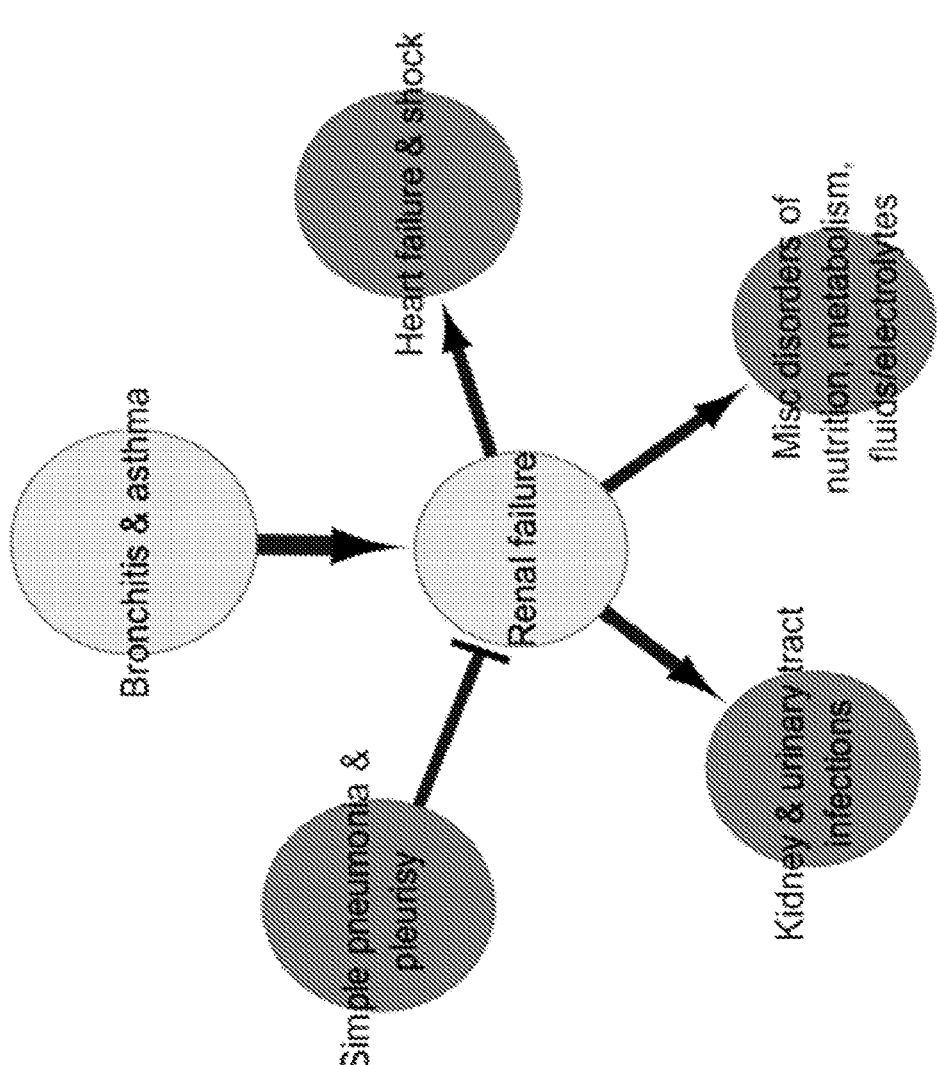
FIG. 17A schematically depicts a sub-network of the relationship network model of FIG. 7 focusing on renal failure and highlighting a connection between bronchitis & asthma and renal failure.
Figure 17B:
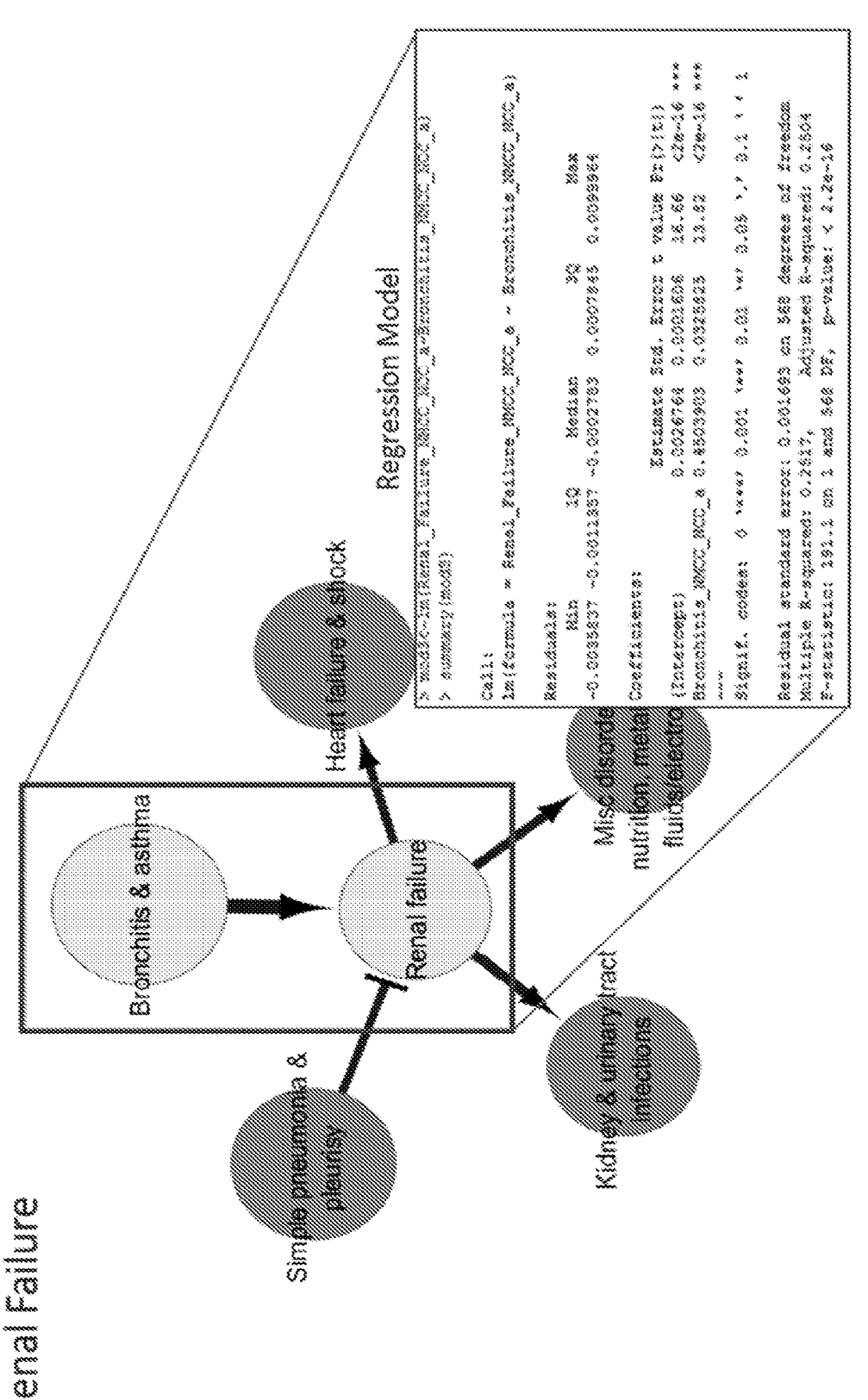
FIG. 17B schematically depicts the connection between bronchitis & asthma and renal failure in the renal failure sub-network and a regression model for the relationship between bronchitis & asthma and renal failure.

The results from the generated network relationship model also lead to the identification of novel interactions. For example, a novel interaction between renal failure and bronchitis & asthma was identified based on the renal failure sub-network. As shown in FIG. 17A, the relationship network model predicted that a diagnosis of bronchitis & asthma leads to or is followed by a diagnosis of renal failure for a statistically significant proportion of patients. The thickness of the arrow indicates that this is a stronger relationship or connection that that between renal failure and any of heart failure & shock, kidney & urinary tract infections, simple pneumonia & pleurisy, and misc. disorders of nutrition, metabolism, and fluids/electrolytes. Because literature on the relationship between renal failure and bronchitis & and asthma is not widely known, or available, this interaction has potential for new discoveries in terms of medication, disease causality and/or order of diagnoses. A regression model was built to identify the strength of interaction, as depicted in FIG. 17B. The regression model indicated that bronchitis and asthma account for ~2.5% (p-value $1.8\times10^{-10}$) of the renal failure data. The p-value is the probability of obtaining a test statistic result at least as extreme as the one that was actually observed assuming the null hypothesis. In this case, the probability of obtaining this data if bronchitis and asthma were completely independent would be $1.8\times10^{-10}$.

FIG. 18A is an association plot of renal failure and bronchitis and asthma. The data represented in FIG. 18A has a p-value of less than $2.22\times10^{-16}$. This plot indicates that bronchitis & asthma and renal failure are not independent and high rates of bronchitis & asthma drives up rates of renal failure. FIG. 18B is a fourfold plot of renal failure with bronchitis & asthma. This plot also shows that high rates of bronchitis & asthma drive up rates of renal failure. The relative risk of renal failure given asthma & bronchitis for a patient was calculated to be 5.13.

A novel hypothesis was developed to link these conditions. Specifically, the hypothesis was that renal failure and/or insufficiency is caused as a side effect of treating asthma and bronchitis. Therefore, when the number of bronchitis and asthma cases increase, the number of renal failure cases increase. This hypothesis is discussed further below.

Bronchitis and asthma are respiratory diseases where narrowing of airways is caused by inflammation. To control symptoms and reduce swelling of airways, many choices of medication are available as illustrated in Table 1 below. The primary ingredient in many of these drugs is a long acting $\beta_2$-adrenergic agonist, and contraindications include hypokalemia. In fact, albuterol ($\beta_2$-agonist) is widely used to treat hyperkalemia in patients with renal failure/insufficiency. Therefore, long term use of drugs containing acting $\beta_2$-agonists can reduce potassium levels leading to hypokalemia. Electrolyte imbalances have been noted in patients treated with $\beta_2$-agonists for asthma.

TABLE 1

Select clinical pharmacology of top 10 asthma drugs in 2011-12. Drug information was obtained from a drug index for prescription drugs. Prescription count information was obtained from a survey by IMS heath.

| | Drug | Prescriptions dispensed (thousands) | Active ingredient(s) | Active ingredient includes long acting β2-adrenergic agonist | Hypokalemia |
|---|---|---|---|---|---|
| 1. | Singular | 28,110 | Montelukast sodium | No | No |
| 2. | Proair HFA | 23,931 | Albuterol sulfate | Yes | Yes |
| 3. | Advair Diskus | 17,534 | Fluticasone propionate and salmeterol | Yes | Yes |

TABLE 1-continued

Select clinical pharmacology of top 10 asthma drugs in 2011-12. Drug
information was obtained from a drug index for prescription drugs. Prescription
count information was obtained from a survey by IMS heath.

| | Drug | Prescriptions dispensed (thousands) | Active ingredient(s) | Active ingredient includes long acting $\beta$2-adrenergic agonist | Hypokalemia |
|---|---|---|---|---|---|
| 4. | Ventolin HFA | 16,272 | Albuterol sulfate | Yes | Yes |
| 5. | Albuterol sulfate | 13,978 | Albuterol sulfate | Yes | Yes |
| 6. | Spiriva Handihaler | 9,416 | Tiotropium | No | No |
| 7. | Flovent HFA | 6,211 | Fluticasone propionate | No | No |
| 8. | Symbicort | 4,962 | Budesonide and formoterol fumarate dihydrate | Yes | Yes |
| 9. | Combivent | 4,251 | Ipratropium bromide and albuterol sulfate | Yes | Yes |
| 10. | Proventil HFA | 4,084 | Albuterol sulfate | Yes | Yes |

Studies have shown that hypokalemia induces renal injury in rats and hypokalemia was observed to cause renal failure in humans. In a study of 55 patients, chronic hypokalemia was accompanied by renal cystogenesis that resulted in scarring and kidney damage leading to renal insufficiency. Other studies have also shown that hypokalemia in patients with renal disease increases the rate of progression to end stage renal disease and increases the rate of mortality. $\beta_2$-agonists may increase aldosterone levels, which in turn has been linked to renal dysfunction. Blocking the function of aldosterone leads to improvement of kidney function.

Figure 19A:
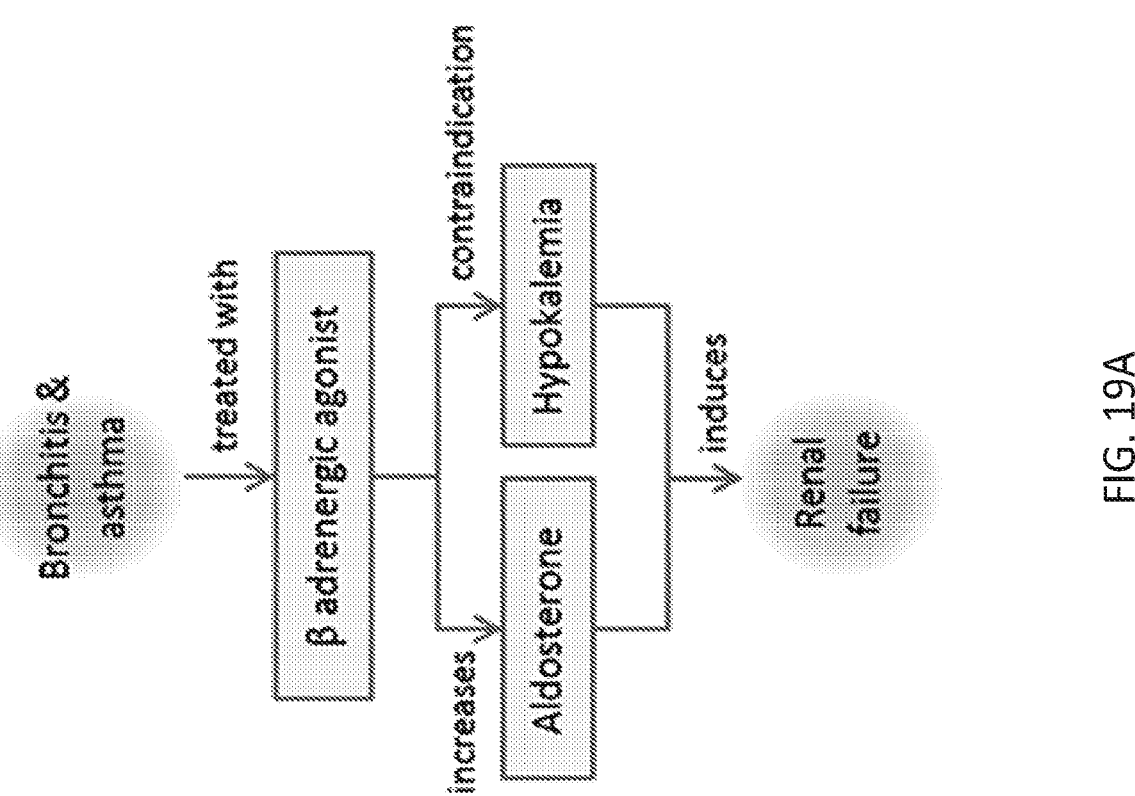
FIG. 19A is a diagram schematically depicting pathways, based on clinical research, explaining a novel connection between bronchitis & asthma and renal failure determined from the renal failure sub-network in Example 1.
Figure 19B:
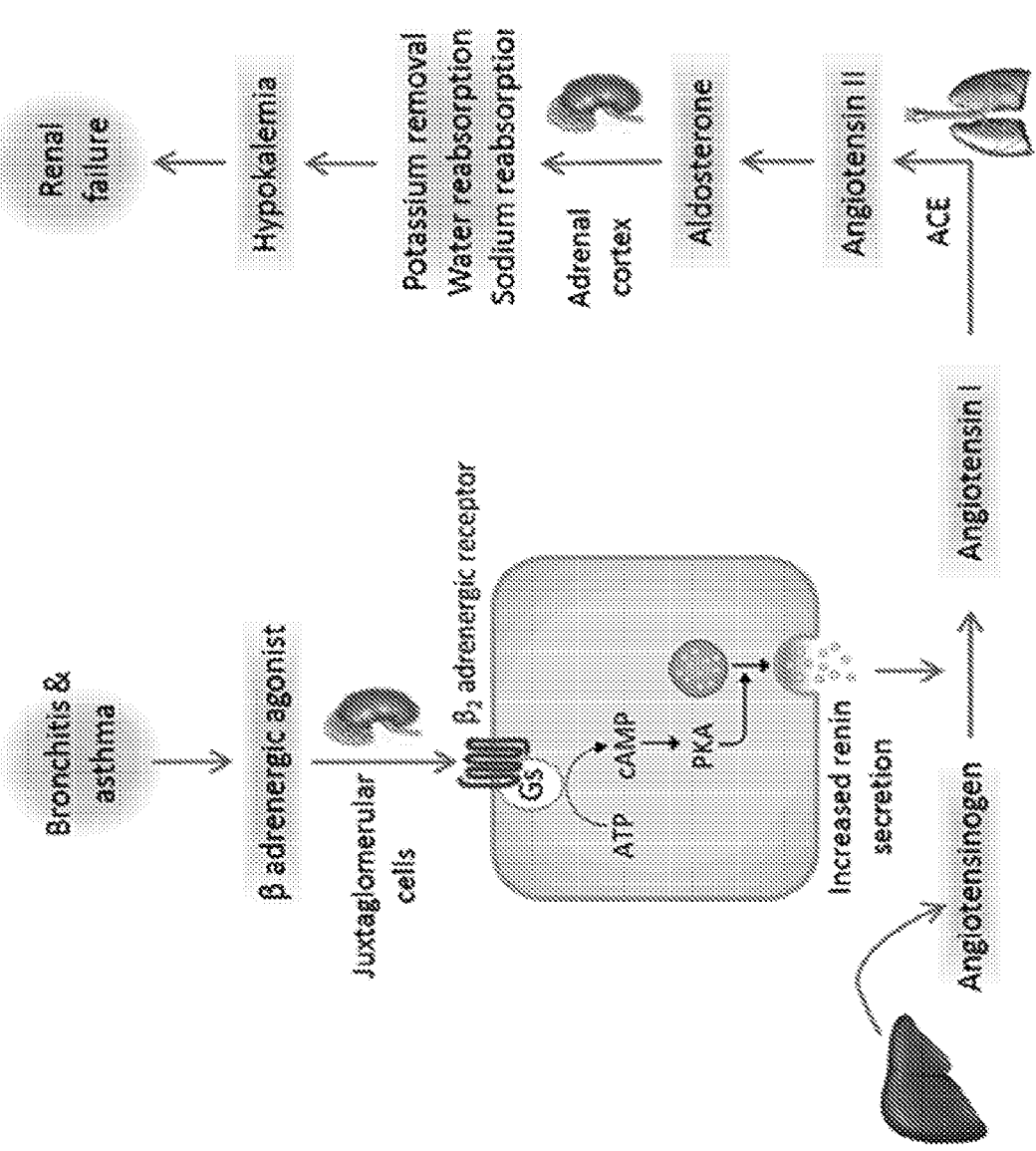
FIG. 19B is a diagram schematically depicting potential molecular mechanisms underlying a novel connection between bronchitis & asthma and renal failure determined from the renal failure sub-network in Example 1.

FIGS. 19A and 19B depict a pathway by which the treatment of bronchitis and asthma could cause renal failure and/or insufficiency supporting the hypothesis and explaining the novel connection between bronchitis and asthma and renal failure. The pathway in FIG. 19A was constructed by linking together published clinical research. FIG. 19B shows potential molecular mechanisms underlying the pathway, which were identified as supporting the clinical findings in the published clinical research. The protein abbreviations used in FIG. 19B are Gs (guanine nucleotide-binding regulatory protein), cAMP (cyclic adenosine monophosphate), PKA (protein kinase A), ACE (angiotensin converting enzyme inhibitor). FIG. 19A schematically depicts a hypothesis connecting bronchitis & asthma and renal failure. Treatment for bronchitis & asthma most frequently involves use of drugs containing long acting $\beta_2$ adrenergic agonists. Long acting $\beta_2$ adrenergic agonists are known to increase aldosterone levels which has been shown to cause renal failure. As per Federal Drug Administration (FDA) labels, hypokalemia is contraindicated for long acting ß2 adrenergic agonists and hypokalemia is a known marker for increased rates of renal failure. FIG. 19B schematically depicts proposed molecular mechanisms linking treatment of asthma & bronchitis with renal failure. Long acting $\beta_2$ adrenergic agonists increase the activity of Gs, which is involved in the production of cAMP that, in turn, increases PKA. This results in increased renin secretion by the juxtaglomerular cells. Renin catalyzes the creation of angiotensin I which is then converted to angiotensin II by ACE activity in lungs. Rising angiotensin II levels cause an increase in aldosterone. In the adrenal cortex of the kidneys, increased aldosterone results in increased potassium removal, water reabsorption and sodium reabsorption, ultimately causing hypokalemia and renal failure. Table 2 includes a listing of published clinical research supporting the pathways and molecular mechanisms shown in FIGS. 19A and 19B.

TABLE 2

Published clinical research supporting the pathway and molecular mechanisms in the hypothesis
regarding the connection between bronchitis and asthma and renal failure.

| Connection | Published Paper |
|---|---|
| hypokalemia and renal dysfunction | Shin-Ichi Suga, M. Ian Phillips, Patricio E. Ray, James A. Raleigh, Carlos P. Vio, Yoon-Goo Kim, Marilda Mazzali, Katherine L. Gordon, Jeremy Hughes, and Richard J. Johnson, "Hypokalemia induces renal injury and alterations in vasoactive mediators that favor salt sensitivity," *Am J. Physical Renal Physiol* 281: F620-F629, 2001. |
| hypokalemia and renal dysfunction | Sirirat Renungjui, Carlos A. Rancol, Waichi Sato, Olena Y. Glushakova, Byron P. Croker, Shin-ichi Suga, Xiaosen Ouyang, Kriang Tungsanga, Takahiko Nakagawa, Richard J. Johnson, and Wei Mu, "Hypokalemia Nephropathy is Associated with Impaired Angiogenesis," *J. Am. Soc. Nephrol.* 19: 125-134, 2008 (doi: 1681/ASN.2007030261). |

TABLE 2-continued

Published clinical research supporting the pathway and molecular mechanisms in the hypothesis
regarding the connection between bronchitis and asthma and renal failure.

| Connection | Published Paper |
|---|---|
| hypokalemia and renal dysfunction | Sirirat Renungjui, Carlos A. Rancol, Waichi Sato, Olena Y. Glushakova, Byron P. Croker, Shin-ichi Suga, Xiaosen Ouyang, Kriang Tungsanga, Takahiko Nakagawa, Richard J. Johnson, and Wei Mu, "Hypokalemia Nephropathy is Associated with Impaired Angiogenesis," *J. Am. Soc. Nephrol.* 19: 125-134, 2008 (doi: 1681/ASN.2007030261). |
| hypokalemia and renal dysfunction | Vicente E. Torres, William F. Young, Jr., Kenneth P. Offord, Robert R. Hattery, "Association of Hypokalemia, Aldosteronism, and Renal Cysts," *N. Engl. J. Med*, 322(6): 345-51 Feb. 8, 1990. |
| hypokalemia and renal dysfunction | Hsiao-Han Wang, Chi-Chih Hung, Daw-Yang Hwang, Mei-Chuan Kuo, Yi-Wen Chiu, Jer-Ming Chang, Jer-Chia Tsai, Shang-Jyh Hwang, Julian F. Seifter, Hung-Chun Chen, "Hypokalemia, Its Contributing Factors and Renal Outcomes in Patients with Chronic Kidney Disease," PLoS ONE 8(7): e67140. doi: 10.1371/journal.pone.0067140, Jul. 2, 2013. |
| hypokalemia and renal dysfunction | John Hayes, Kamyar Kalantar-Zadeh, Jun F. Fu, Sharon Turban, John E. Anderson, Csaba P. Kovesdy, "Associate of Hypo- and Hyperkalemia with Disease Progression and Mortality in Males with Chronic Kidney Disease: The Role of Race," *Nephron Clin Pract* 2012; 120: c8-c16. |
| long acting β₂-adrenergic agonist and aldosterone stimulation | Evelyn A. Millar, John M. C. Connel, Neil C. Thomson, "The Effect of Nebulized Albuterol on the Activity of the Renin-Angiotensin System in Asthma," CHEST 1997; 111: 71-74. |
| long acting β₂-adrenergic agonist and aldosterone stimulation | Millar E A, McInnes G T, Thomson N C "Investigation of the mechanism of beta 2-agonist-induced activation of the renin-angiotensin system," *Clin Sci* (Lond) 1995 April; 88(4): 433-7. |
| aldosterone stimulation and renal dysfunction | Murray Epstein, "Aldosterone and the hypertensive kidney: its emerging role as a mediator of progressive renal dysfunction: a paradigm shift," *Journal of Hypertension* May 2001; 19(5): 829-842. |
| aldosterone stimulation and renal dysfunction | Akio Nakamura, Ryo Niimi, Akira Imaizumi, Yukishige Yanagawa, "Renal Effects of Beta₂-Adrenoceptor Agonist and the Clinical Analysis in Children," *Pediatric Research*, 61(1): 129-33, 2007. |
| aldosterone stimulation and renal dysfunction | Ulrich Wenzel, "Aldosterone and progression of renal disease," *Current Opinion in Nephrology and Hypertension* 2008, 17: 44-50. |

The total cost to treat renal disease in patents in this CMS dataset, which includes the 3000 hospitals enrolled in Inpatient Prospective Payment Systems (IPPS), was $2.3 billion. This CMS dataset represented 60% of total Medicare discharges. Therefore, the total Medicare cost for this diagnosis code alone for the year of 2011 would have been $3.83 billion. Of this cost, 2.5% would be attributed to be side effects of drugs used to treat bronchitis and asthma. Further investigation and modification of treatment guidelines for asthma/bronchitis based on the relationship between renal failure and bronchitis and asthma determined using the relationship network model of Example 1 may not only lead to better patient care, but also considerable cost savings. For example, with patient level data, it is possible to identify patients with high risk for renal side effects based on medical history and genetic factors. For high risk patients, alternative treatment strategies, or monitoring of renal function, can result in better outcomes for patients and lower costs for payers like Medicare. Such improvements to care can be incorporated into the clinic, through clinical decision support systems, by integrating patient electronic health records with a knowledge base, to provide personalized patient care guidelines.

Figure 20:
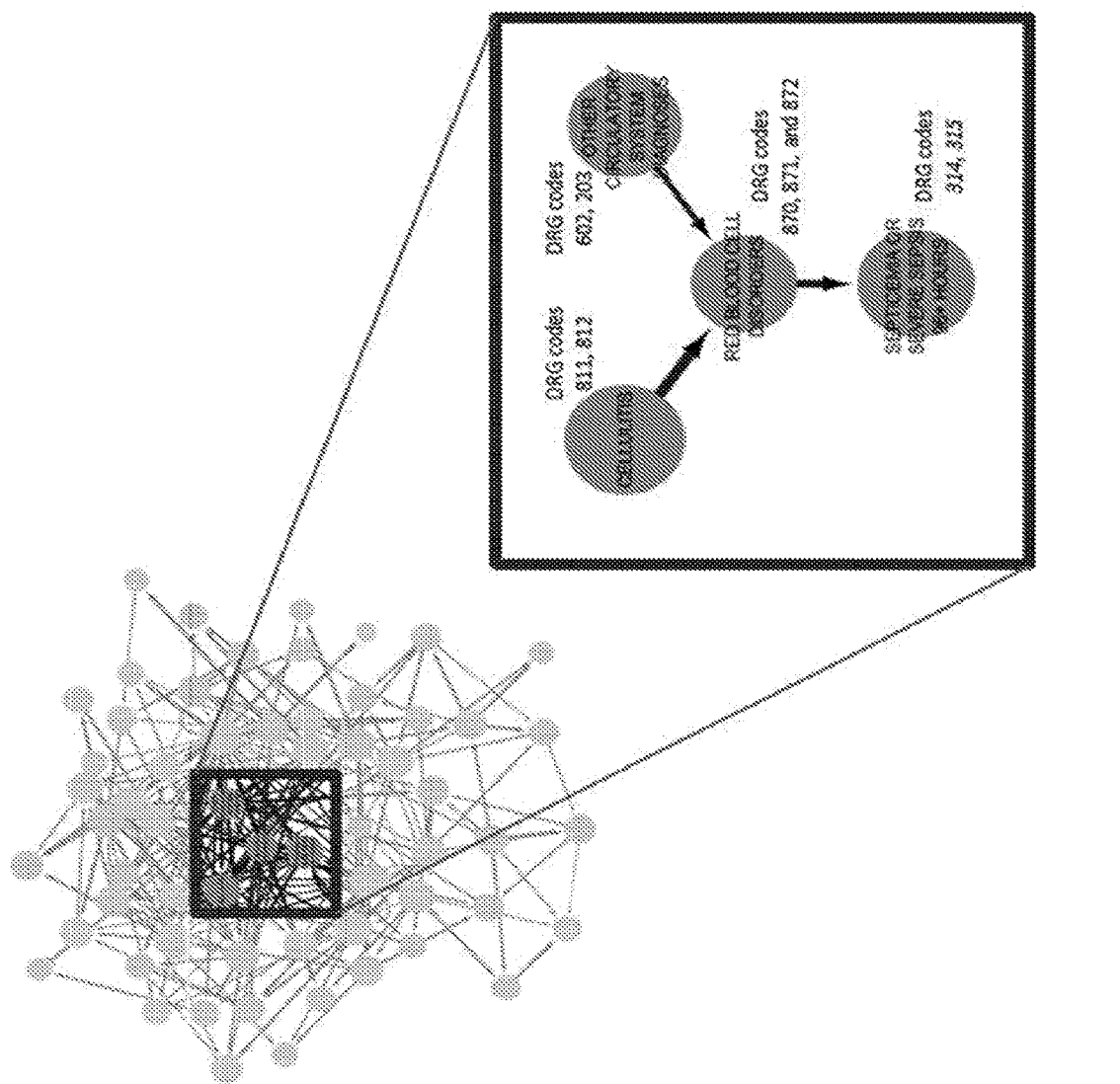
FIG. 20 schematically depicts the relationship network model of Example 1 and the selected red blood cell disorders sub-network of Example 2.

Example 2—Relationship Network Model Generated from CMS Data: Sub-Network of Red Blood Cell (RBC) Disorders A sub-network centered on Red Blood Cell (RBC) disorders was also selected from the generated relationship network model described in Example 1. FIG. 20 schematically depicts the relationship network model and the selected RBC disorders sub-network. Another novel interaction was determined from RBC disorders sub-network.

The DRG code for RBC disorders covers anemia (caused by nutrition, genetics and comorbidity), reaction from transfusions (ABO, Rh incompatibility) and cytopenias. All related diagnoses were taken into account in analyses linking RBC disorders to other diagnoses.

The RBC disorders sub-network indicated that a diagnosis of cellulitis lead to or was followed by a diagnosis of an RBC disorder in a statistically significant proportion of patients. When cellulitis is untreated, bacteria from the infection enter the blood stream and cause septicemia. Previous studies have shown that sepsis changes RBC morphology and rheology. It was hence plausible that an increase in diagnoses of cellulitis causes an increase in diagnoses of RBC disorders.

The RBC disorders sub-network indicated that a diagnosis of an RBC disorder lead to or was followed by a diagnosis of septicemia or severe sepsis in a statistically significant proportion of patients. Sepsis is likely in surgery patients that in turn are likely to have intravenous infusions. Numerous or prolonged intravenous infusions can cause pancytopenia thereby linking diagnosis of RBC disorders with septicemia.

The RBC disorder sub-network also indicated that an "other circulatory system diagnosis" lead to or was followed by a diagnosis of an RBC disorder in a statistically significant proportion of patients. The Circulatory system code (i.e., other circulatory system diagnoses) includes infection and abnormalities of cardiac tissue, and complications of heart surgery (bypass, placement of shunts, implants, and valves). A possible connection between circulatory disorders and RBC disorders involves hemolytic anemia from prosthetic valves. Specifically, iron deficiency anemia, an RBC disorder, can lead to rapid or irregular heartbeat, which can cause an enlarged heart or heart failure.

Findings such as the novel interactions identified in Example 1 and 2 can have a significant impact on both patients and providers. An important aspect of efficient healthcare delivery is forecasting resource requirements, identification of strategies to maximize resource utilization and availability of provider options. Currently, only some parts of Medicare billing data such as case mix index are used for planning. Augmenting such data with advanced statistical analyses on billing data can dramatically enhance the efficiency of healthcare management and create significant savings to the healthcare system. The results show a new perspective on use of advanced analyses of Big Data and, more importantly, demonstrate that the methodology described herein can be effectively used to extract actionable information from Big Data. Inferred BNs, which are relationship network models in accordance with some embodiments, can also be analyzed to improve patient care by identification of adverse drug interactions, comorbidities and disease causality. The Examples presented herein illustrate how embodiments can be used to understand and making sense of the voluminous, convoluted data sets to identify novel interactions and generate an actionable output for healthcare analytics and in-kind, healthcare economics.

In Examples 1 and 2, a meaningful relationship network model was built representing interactions between diagnoses based on numbers of discharges, in accordance with an embodiment. The relationship network model was generated using entirely data-driven methods completely unbiased by current knowledge or hypotheses. Results from the relationship network model were validated using literature support. The Examples illustrate that even a relatively small scale analysis on low resolution data resulted in the identification of novel interactions that have clinical impact.

The Example results illustrate how purely data-driven methodology in analysis of Big Data, in accordance with embodiments described herein, could be used in healthcare to expedite medical research and improve patient care by providing unique insights. The Example results show a new perspective on application of advanced analyses in Big Data and, more importantly, demonstrate that relationship network models formed using Bayesian network algorithms, can be effectively used to extract actionable information.

In this manner, the healthcare analysis system and methods disclosed herein can be used to analyze large datasets and to glean novel insights into the relationships of the data points in the datasets. Such analysis can be performed on datasets containing detailed DRG codes information, patient level claims information, patient clinical information such as diagnoses, medication, longitudinal data, clinical test results, and the like. Such analysis can be beneficial to the pharmaceutical industry in terms of prescription recommendations, side effects and toxicity analysis, drug interactions, drug repositioning, patient groups for drug trials, and the like. Such analysis can be beneficial to the hospital industry in terms of clinical decision support systems, improvement of outcomes for outcome based payments, improvement of standard of care, and the like.

Certain embodiments are described herein as including logic or a number of components, modules, or mechanisms. Modules may constitute either software modules (e.g., code embodied on a machine-readable medium or in a transmission signal) or hardware modules. A hardware module is a tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA), an application-specific integrated circuit (ASIC), or a Graphics Processing Unit (GPU)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired) or temporarily configured (e.g., programmed) to operate in a certain manner and/or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least some of the operations of a method may be performed by one or processors or processor-implemented modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., APIs).

Example embodiments may be implemented in digital electronic circuitry, or in computer hardware, firmware, software, or in combinations of them. Example embodiments may be implemented using a computer program product, for example, a computer program tangibly embodied in an information carrier, for example, in a machine-readable medium for execution by, or to control the operation of, data processing apparatus, for example, a programmable processor, a computer, or multiple computers.

A computer program can be written in any form of programming language, including compiled or interpreted languages, and it can be deployed in any form, including as a stand-alone program or as a module, subroutine, or other unit suitable for use in a computing environment. A computer program can be deployed to be executed on one computer or on multiple computers at one site or distributed across multiple sites and interconnected by a communication network.

In example embodiments, operations may be performed by one or more programmable processors executing a computer program to perform functions by operating on input data and generating output. Method operations can also be performed by, and apparatus of example embodiments may be implemented as, special purpose logic circuitry (e.g., a FPGA or an ASIC).

The computing system can include clients and servers. A client and server are generally remote from each other and typically interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware may be a design choice. Below are set out hardware (e.g., machine) and software architectures that may be deployed, in various example embodiments.

Figure 21:
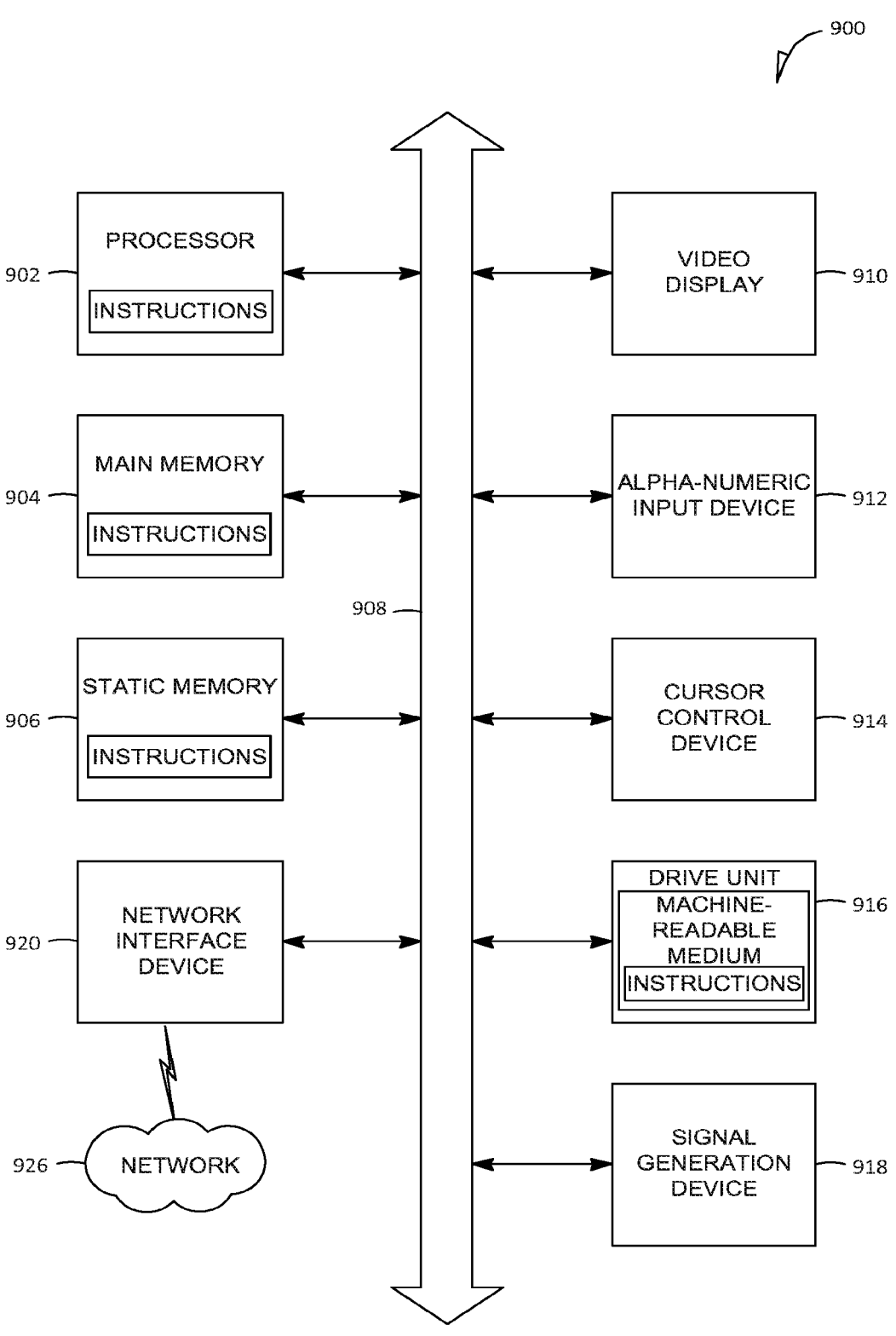
FIG. 21 is a block diagram of a computing device that may be used to implement some embodiments of healthcare analysis systems and methods described herein.

FIG. 21 is a block diagram of machine in the example form of a computer system 900 within which instructions, for causing the machine (e.g., client device 110, 115, 120, 125; server 135; database server(s) 140; database(s) 130) to perform any one or more of the methodologies discussed herein, may be executed. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a PDA, a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 900 includes a processor 902 (e.g., a central processing unit (CPU), a multi-core processor, and/or a graphics processing unit (GPU)), a main memory 904 and a static memory 906, which communicate with each other via a bus 908. The computer system 900 may further include a video display unit 910 (e.g., a liquid crystal display (LCD), a touch screen, or a cathode ray tube (CRT)). The computer system 900 also includes an alphanumeric input device 912 (e.g., a physical or virtual keyboard), a user interface (UI) navigation device 914 (e.g., a mouse), a disk drive unit 916, a signal generation device 918 (e.g., a speaker) and a network interface device 920.

The disk drive unit 916 includes a machine-readable medium 922 on which is stored one or more sets of instructions and data structures (e.g., software) 924 embodying or used by any one or more of the methodologies or functions described herein. The instructions 924 may also reside, completely or at least partially, within the main memory 904, static memory 906, and/or within the processor 902 during execution thereof by the computer system 900, the main memory 904 and the processor 902 also constituting machine-readable media.

While the machine-readable medium 922 is shown in an example embodiment to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present invention, or that is capable of storing, encoding or carrying data structures used by or associated with such instructions. The term "machine-readable medium" shall accordingly be taken to include, but not be limited to, solid-state memories, and optical and magnetic media. Specific examples of machine-readable media include non-volatile memory, including by way of example, semiconductor memory devices (e.g., Erasable Programmable Read-Only Memory (EPROM), Electrically Erasable Programmable Read-Only Memory (EEPROM)) and flash memory devices: magnetic disks such as internal hard disks and removable disks: magneto-optical disks: and CD-ROM and DVD-ROM disks.

The instructions 924 may further be transmitted or received over a communications network 926 using a transmission medium. The instructions 924 may be transmitted using the network interface device 920 and any one of a number of well-known transfer protocols (e.g., HTTP).

Examples of communication networks include a LAN, a WAN, the Internet, mobile telephone networks, Plain Old Telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software.

Although the present invention has been described with reference to specific example embodiments, it will be evident that various modifications and changes may be made to these embodiments without departing from the broader spirit and scope of the invention. Accordingly, the specification and drawings are to be regarded in an illustrative rather than a restrictive sense.

It will be appreciated that, for clarity purposes, the above description describes some embodiments with reference to different functional units or processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

Although an embodiment has been described with reference to specific example embodiments, it will be evident that various modifications and changes may be made to these embodiments without departing from the broader spirit and scope of the invention. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be used and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended: that is, a system, device, article, or process that includes elements in addition to those listed after such a term in a claim are still deemed to fall within the scope of that claim. Moreover, in the following claims, the terms "first," "second," and "third" and so forth are used merely as labels, and are not intended to impose numerical requirements on their objects.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

The invention claimed is:

1. A computer-implemented method for generating a causal relationship network model based on patient data, the method comprising:

accessing or obtaining normalized data for a plurality of variables, the normalized data corresponding to a plurality of patients and including diagnostic information and/or treatment information for each patient, wherein, for each patient, the normalized data includes more than one variable; and generating a causal relationship network model relating the plurality of variables based on the normalized data for the plurality of patients using a programmed computing system including storage holding network model building code and a plurality of processors configured to execute the network model building code, the generating including creating and evolving an ensemble of probabilistic networks based on the normalized data for the plurality of patients, the causal relationship network model including variables related to a plurality of medical conditions, and the ensemble of probabilistic networks created and evolved in parallel on the plurality of processors.

2. The method of claim 1, wherein the causal relationship network model includes relationships indicating one or more predictors for each of the plurality of medical conditions.

3. The method of claim 1, wherein the accessed or obtained normalized data is not pre-selected as being relevant to one or more of the plurality of medical conditions.

4. The method of claim 1, wherein the plurality of patients includes a first subset of patients each having data indicating a diagnosis of a medical condition in the patient, and includes a second subset of patients each having data that does not indicate a diagnosis of the medical condition in the patient.

5. The method of claim 1, further comprising:

receiving updated or additional data corresponding to one or more of the plurality of patients or corresponding to one or more additional patients; and updating the causal relationship network model based on the updated or additional data.

6. The method of claim 1, wherein the causal relationship network model is generated based solely on the normalized data.

7. The method of claim 1, further comprising:

determining a sub-network from the causal relationship network model, one or more variables in the sub-network associated with a selected medical condition or with a selected drug; and probing relationships in the sub-network to determine one or more predictors for the selected medical condition or for the selected drug.

8. The method of claim 7, wherein the one or more predictors for the selected medical condition indicate a medical condition co-occurring with the selected medical condition.

9. The method of claim 7, wherein the extent of the sub-network is determined based on the one or more variables associated with the selected medical condition or with the selected drug and the strength of the relationships between the one or more variables and other variables in the causal relationship network model.

10. The method of claim 7, wherein the sub-network includes the one or more variables associated with the selected medical condition or with the selected drug, a first set of additional variables each having a first degree relationship with the one or more variables, and a second set of additional variables each having second degree relationship with the one or more variables.

11. The method of claim 7, wherein at least one of the one or more predictors is newly identified as a predictor for the medical condition or is newly identified as a predictor relevant to the selected drug.

12. The method of claim 7, further comprising:

displaying the one or more predictors in a user interface, the displaying including a graphical representation of the one or more variables, the one or more predictors, and relationships among the one or more variables and the one or more predictors.

13. The method of claim 7, further comprising displaying a graphical representation of the sub-network in a user interface.

14. The method of claim 7, further comprising ranking the one or more predictors based on strength of relationships between the one or more variables and the one or more predictors.

15. The method of claim 7, wherein the one or more predictors relevant to the selected drug indicates a drug administered in conjunction with the selected drug.

16. The method of claim 7, wherein the one or more predictors indicate an adverse drug interaction between the selected drug and one or more other drugs.

17. The method of claim 1, wherein the causal relationship network model is generated based on between 50 variables and 1,000,000 variables.

18. The method of claim 1, wherein the normalized data includes information from patient electronic health records.

19. The method of claim 1, wherein generating the causal relationship network model relating the plurality of variables based on the normalized data for the plurality of patients comprises:

creating a list of network fragments, each network fragment including two or more variables connected by one or more relationships, and determining a probabilistic score associated with each network fragment based on the normalized data;

creating an ensemble of trial networks that is an ensemble of Bayesian networks, each trial network constructed from a different subset of the list of network fragments; and globally optimizing the ensemble of trial networks by evolving each trial network through local transformations in parallel using the plurality of processors to produce a consensus causal relationship network model.

\* \* \* \* \*